US012390215B2

(12) United States Patent
Asherov et al.

(10) Patent No.: US 12,390,215 B2
(45) Date of Patent: Aug. 19, 2025

(54) SUTURING WITH AN ENDOLUMINAL GASTROPLASTY DEVICE

(71) Applicant: Nitinotes Ltd., Caesarea (IL)

(72) Inventors: Asaf Asherov, Pardes Hanna-Karkur (IL); Raz Bar-On, Hadera (IL); Gilad Heftman, Pardes Hana Karkur (IL); Raz Ben Yaakov, D.N. Hof HaCarmel (IL); Marina Dror, Haifa (IL); Dmitry Golom, Haifa (IL)

(73) Assignee: Nitinotes Ltd., Caesarea (IL)

( * ) Notice: Subject to any disclaimer, the term of this patent is extended or adjusted under 35 U.S.C. 154(b) by 380 days.

(21) Appl. No.: 17/802,165

(22) PCT Filed: Feb. 23, 2021

(86) PCT No.: PCT/IL2021/050208
§ 371 (c)(1),
(2) Date: Aug. 25, 2022

(87) PCT Pub. No.: WO2021/171290
PCT Pub. Date: Sep. 2, 2021

(65) Prior Publication Data
US 2023/0355232 A1    Nov. 9, 2023

Related U.S. Application Data

(60) Provisional application No. 62/981,573, filed on Feb. 26, 2020.

(51) Int. Cl.
*A61B 17/04* (2006.01)
*A61B 17/06* (2006.01)
(Continued)

(52) U.S. Cl.
CPC .... *A61B 17/0487* (2013.01); *A61B 17/06066* (2013.01); *A61B 17/0625* (2013.01);
(Continued)

(58) Field of Classification Search
CPC ............ A61B 17/0401; A61B 17/0487; A61B 17/06066; A61B 17/0625;
(Continued)

(56) References Cited

U.S. PATENT DOCUMENTS 5,545,148 A    8/1996  Wurster
5,947,983 A  * 9/1999  Solar .................. A61B 17/0469
                                                              606/144

(Continued)

FOREIGN PATENT DOCUMENTS

CN    1822794       8/2006
CN    101044996    10/2007
(Continued)

OTHER PUBLICATIONS

Notification of Office Action and Search Report Dated Sep. 19, 2024 From the State Intellectual Property Office of the People's Republic of China Re. Application No. 202180027964.3 and its Machine Translation and English Summary. (20 Pages).

(Continued)

*Primary Examiner* — Kathleen S Holwerda

(57) ABSTRACT

Suture clips configured to be placed in a predetermined path of a suturing needle that advances through a device inserted to a body cavity, and remotely operated from that position to secure and clamp suturing. In some embodiments, a suture tightening device is placed in the predetermined path and configured to capture the suture and shorten a length of tissue-engaged suture by pulling on the suture. In some embodiments, sensors are placed along the needle path and used to provide an indication of needle position and/or status.

19 Claims, 13 Drawing Sheets

(51) Int. Cl.
  *A61B 17/062* (2006.01)
  *A61F 5/00* (2006.01)
  *A61B 17/00* (2006.01)
  *A61B 90/00* (2016.01)

(52) U.S. Cl.
  CPC .. *A61F 5/0086* (2013.01); *A61B 2017/00026* (2013.01); *A61B 2017/00039* (2013.01); *A61B 2017/00561* (2013.01); *A61B 2017/0488* (2013.01); *A61B 2017/0496* (2013.01); *A61B 2017/0498* (2013.01); *A61B 2017/06076* (2013.01); *A61B 2090/064* (2016.02)

(58) Field of Classification Search
  CPC ........... A61B 2017/00026; A61B 2017/00039; A61B 2017/00561; A61B 2017/0488; A61B 2017/0496; A61B 2017/0498; A61B 2017/06076; A61B 17/0469; A61B 17/0491; A61F 5/0086
  See application file for complete search history.

(56) References Cited

U.S. PATENT DOCUMENTS

| | | | |
|---|---|---|---|
| 6,558,400 | B2 | 5/2003 | Deem et al. |
| 7,083,629 | B2 | 8/2006 | Weller et al. |
| 7,674,276 | B2 * | 3/2010 | Stone ............... A61B 17/0401 606/103 |
| 7,766,925 | B2 * | 8/2010 | Stokes ............... A61B 1/005 606/139 |
| 7,779,845 | B2 | 8/2010 | Ortiz |
| 7,896,890 | B2 | 3/2011 | Ortiz et al. |
| 8,075,573 | B2 | 12/2011 | Gambale et al. |
| 8,906,039 | B2 | 12/2014 | Crainich |
| 8,906,040 | B2 | 12/2014 | Fililpi et al. |
| 8,939,902 | B2 | 1/2015 | Roth et al. |
| 8,992,570 | B2 | 3/2015 | Gambale et al. |
| 9,149,270 | B2 | 10/2015 | Fogel |
| 2002/0107530 | A1 | 8/2002 | Sauer et al. |
| 2003/0171760 | A1 | 9/2003 | Gambalc |
| 2003/0229361 | A1 * | 12/2003 | Jackson ............. A61B 17/0487 606/144 |
| 2004/0158125 | A1 | 8/2004 | Aznoian et al. |
| 2005/0192629 | A1 * | 9/2005 | Saadat ................. A61F 5/0076 606/221 |
| 2006/0212048 | A1 | 9/2006 | Crainoch |
| 2006/0253126 | A1 | 11/2006 | Bjerken |
| 2006/0253127 | A1 | 11/2006 | Bjerken |
| 2006/0282094 | A1 | 12/2006 | Stokes et al. |
| 2007/0055292 | A1 | 3/2007 | Ortiz et al. |
| 2007/0129735 | A1 | 6/2007 | Filipi |
| 2008/0249404 | A1 | 10/2008 | Mikkaichi et al. |
| 2008/0275473 | A1 | 11/2008 | Filipi et al. |
| 2012/0022560 | A1 | 1/2012 | Ferreira |
| 2012/0204865 | A1 | 8/2012 | Filipi et al. |
| 2014/0155915 | A1 | 6/2014 | Mikkaichi et al. |
| 2017/0304099 | A1 | 10/2017 | Keren et al. |
| 2022/0079577 | A1 | 3/2022 | Bar-On et al. |
| 2022/0233189 | A1 | 7/2022 | Azar |

FOREIGN PATENT DOCUMENTS

| | | |
|---|---|---|
| CN | 101209214 | 7/2008 |
| CN | 102405022 | 4/2012 |
| CN | 106999177 | 8/2017 |
| CN | 115484874 | 12/2022 |
| EP | 2861159 | 2/2018 |
| EP | 3476325 | 5/2019 |
| EP | 2785497 | 10/2022 |
| JP | 2004-500206 | 1/2004 |
| JP | 2004-514462 | 5/2004 |
| JP | 2005-161050 | 6/2005 |
| JP | 2007-500575 | 1/2007 |
| JP | 2007-275577 | 10/2007 |
| JP | 2008-132328 | 6/2008 |
| JP | 2008-161686 | 7/2008 |
| JP | 2009-532074 | 9/2009 |
| JP | 2012-506756 | 3/2012 |
| JP | 2017-533791 | 11/2017 |
| KR | 10-1857507 | 5/2018 |
| WO | WO 01/66001 | 9/2001 |
| WO | WO 2004/103189 | 12/2004 |
| WO | WO 2007/098212 | 8/2007 |
| WO | WO 2008/069816 | 6/2008 |
| WO | WO 2009/084436 | 7/2009 |
| WO | WO 2010/050910 | 5/2010 |
| WO | WO 2016/056016 | 4/2016 |
| WO | WO 2020/144693 | 7/2020 |
| WO | WO 2021/171290 | 9/2021 |

OTHER PUBLICATIONS

Communication Pursuant to Article 94(3) EPC Dated Dec. 17, 2024 From the European Patent Office Re. Application No. 21760195.4. (3 Pages).
Notification of Office Action Dated Dec. 17, 2024 From the National Intellectual Property Administration of the People's Republic of China Re. Application No. 202080019590.6 and its Machine Translation Into English. (9 Pages).
Restriction Official Action Dated Apr. 9, 2024 From the US Patent and Trademark Office Re. U.S. Appl. No. 17/421,444. (6 pages).
Notice of Reason(s) for Rejection Dated From the Japan Patent Office Re. Application No. 2021-540026 and its Translation Into English. (21 Pages).
Notification of Office Action Dated Jan. 11, 2024 From the National Intellectual Property Administration of the People's Republic of China Re. Application No. 202080019590.6 and its Machine Translation Into English. (9 Pages).
Notice of Reasons for Rejection Dated Oct. 22, 2024 From the Japan Patent Office Re. Application No. 2022-550975 and its Translation Into English. (11 Pages).
English Summary Dated Aug. 6, 2024 of Notification of Office Action Dated Jul. 22, 2024 From the National Intellectual Property Administration of the People's Republic of China Re. Application No. 202080019590.6. (5 Pages).
International Preliminary Report on Patentability Dated Jul. 22, 2021 From the International Bureau of WIPO Re. Application No. PCT/IL2020/050041. (10 Pages).
International Search Report and the Written Opinion Dated Apr. 2, 2020 From the International Searching Authority Re. Application No. PCT/IL2020/050041. (16 Pages).
International Search Report and the Written Opinion Dated May 27, 2021 From the International Searching Authority Re. Application No. PCT/IL2021/050208. (25 Pages).
Invitation to Pay Additional Fees and Communication Relating to the Results of the Partial International Search Dated May 2, 2021 From the International Searching Authority Re. Application No. PCT/IL2021/050208. (5 Pages).
Supplementary European Search Report and the European Search Opinion Dated Sep. 21, 2022 From the European Patent Office Re. Application No. 20738264.9. (11 pages).
Official Action Dated Aug. 15, 2024 From the US Patent and Trademark Office Re. U.S. Appl. No. 17/421,444. (54 pages).
Machine Translation Dated Jul. 30, 2024 of Notification of Office Action and Search Report Dated Jul. 22, 2024 From the National Intellectual Property Administration of the People's Republic of China Re. Application No. 202080019590.6. (11 Pages).
Notification of Office Action and Search Report Dated Jul. 22, 2024 From the National Intellectual Property Administration of the People's Republic of China Re. Application No. 202080019590.6. (11 Pages).
English Summary Dated Jan. 29, 2024 of Notification of Office Action Dated Jan. 11, 2024 From the National Intellectual Property Administration of the People's Republic of China Re. Application No. 202080019590.6 (2 Pages).

(56) References Cited

OTHER PUBLICATIONS

Notice of Reason(s) for Rejection Dated Mar. 12, 2024 From the Japan Patent Office Re. Application No. 2021-540026 and its Translation Into English. (5 Pages).
Supplementary European Search Report and the European Search Opinion Dated Mar. 20, 2024 From the European Patent Office Re. Application No. 21760195.4. (9 Pages).
Notice of Reason(s) for Rejection Dated Apr. 30, 2025 From the Japan Patent Office Re. Application No. 2022-550975 and Its Translation Into English. (7 Pages).

* cited by examiner

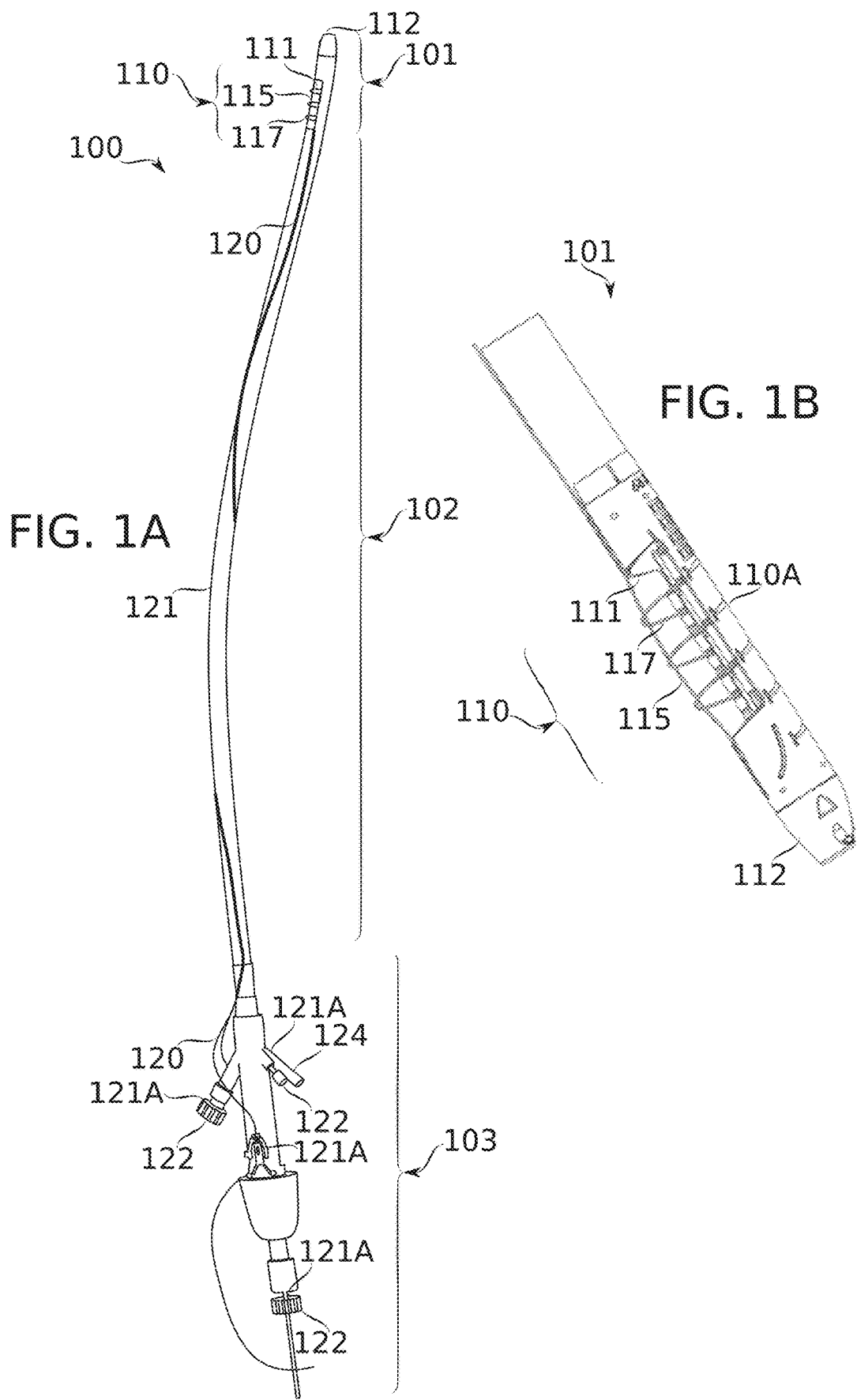

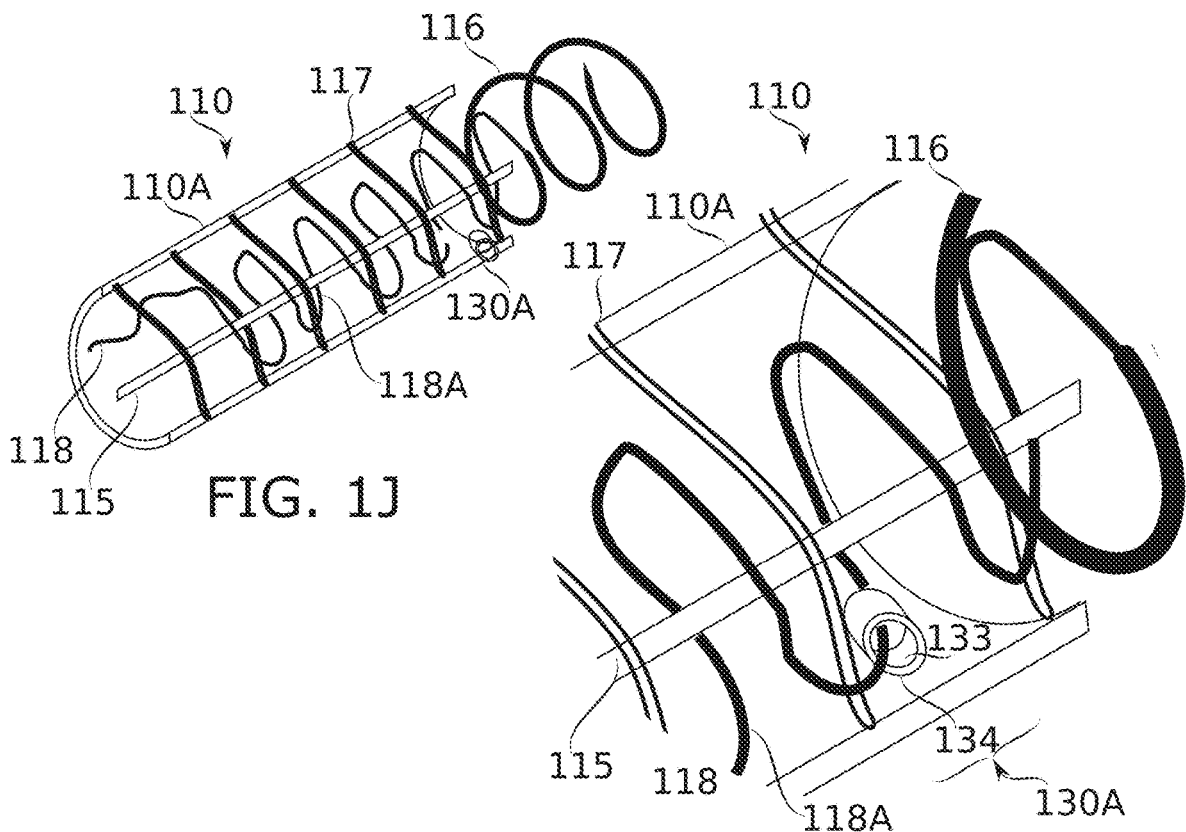
FIG. 1J
FIG. 1K
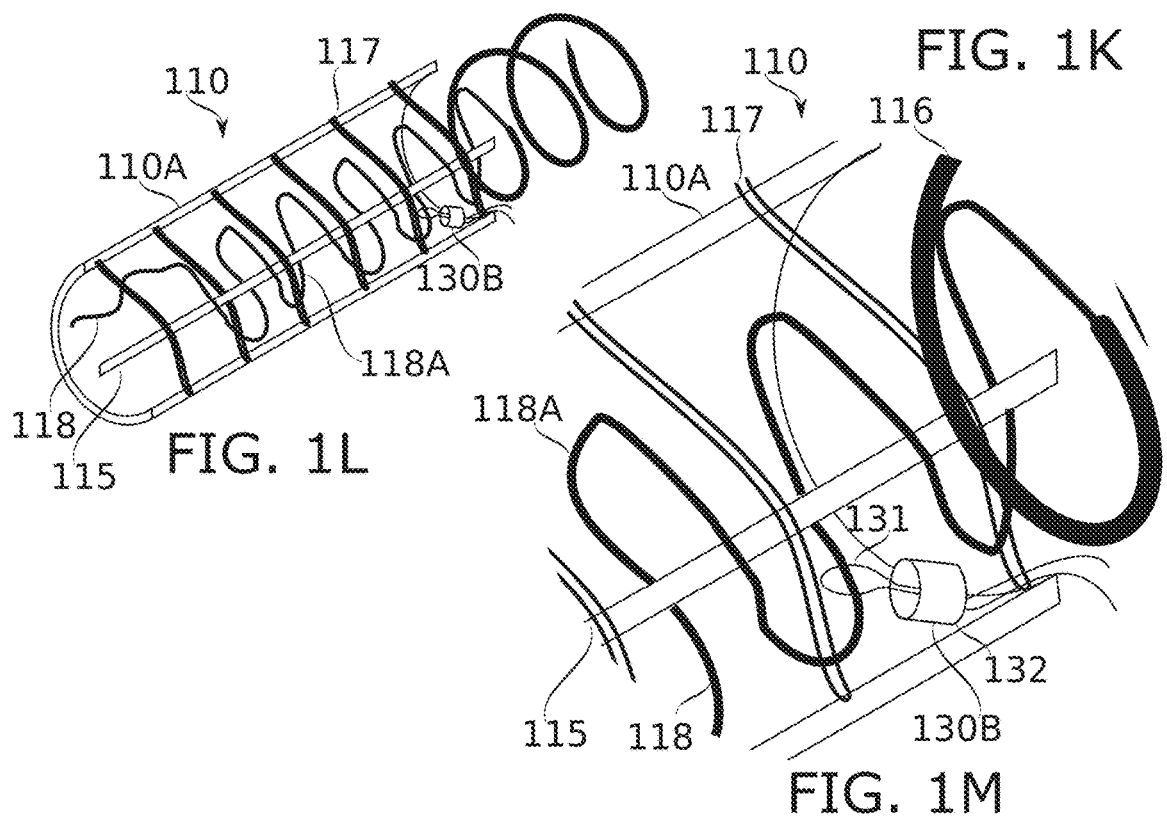
FIG. 1L
FIG. 1M

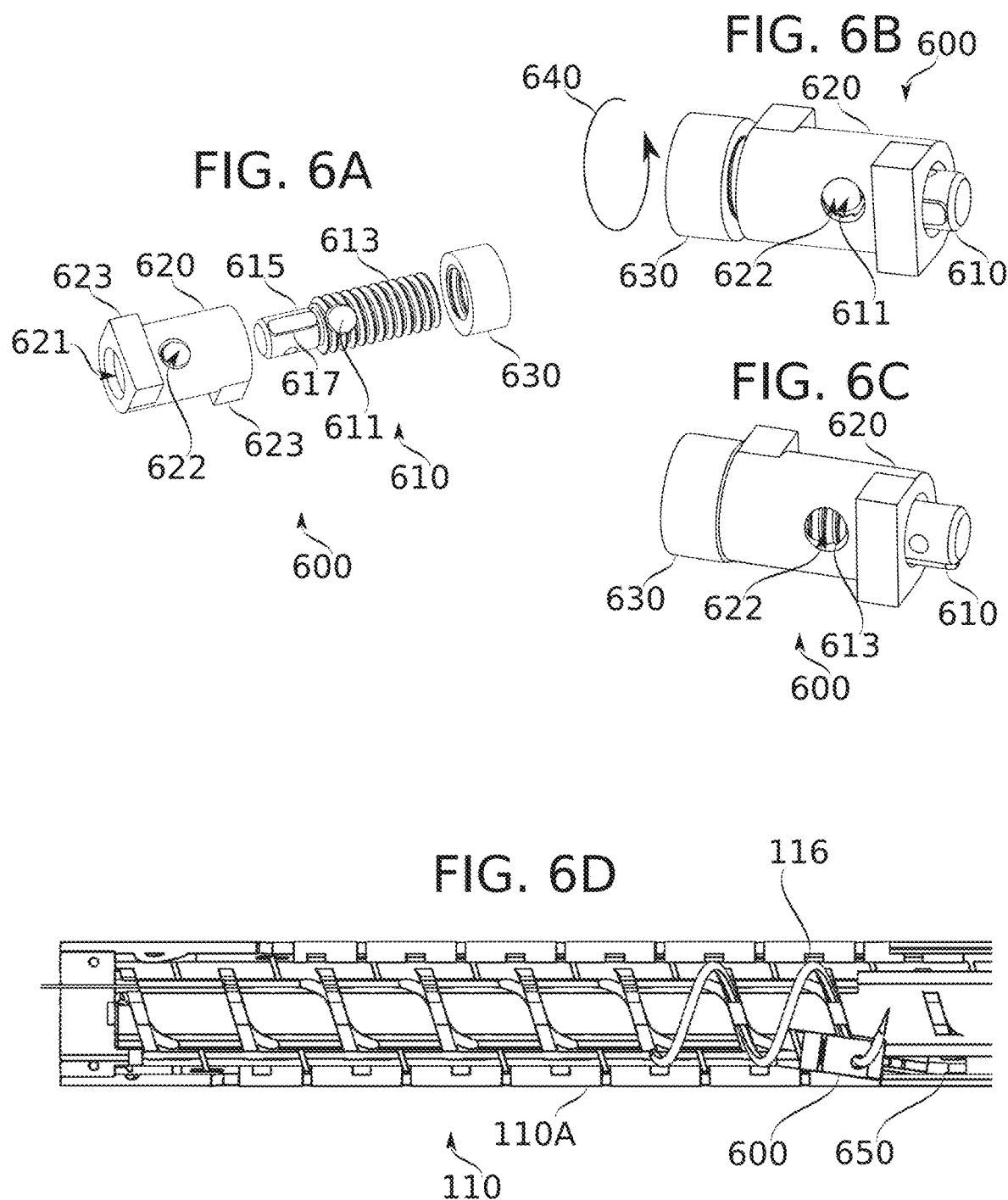

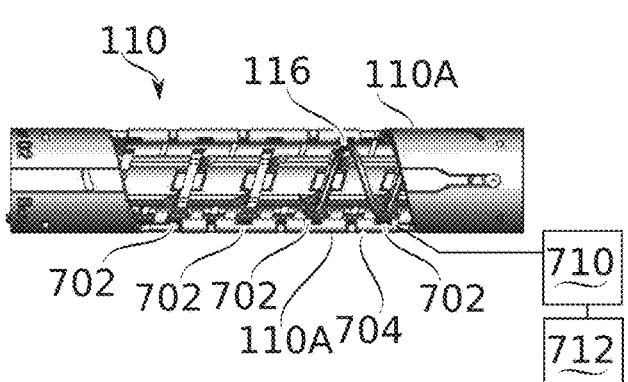
FIG. 7A
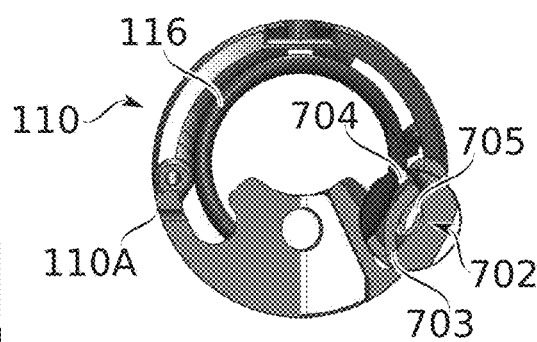
FIG. 7B
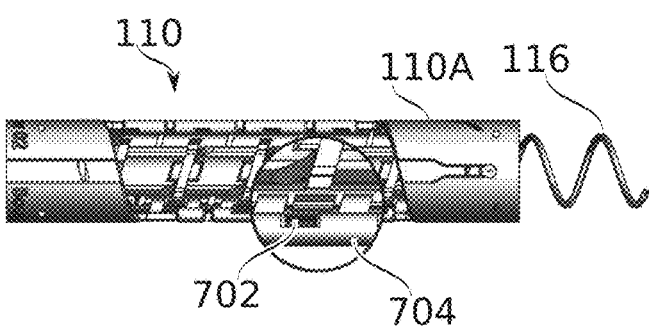
FIG. 7C
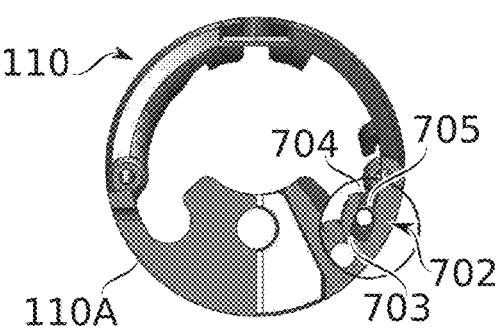
FIG. 7D
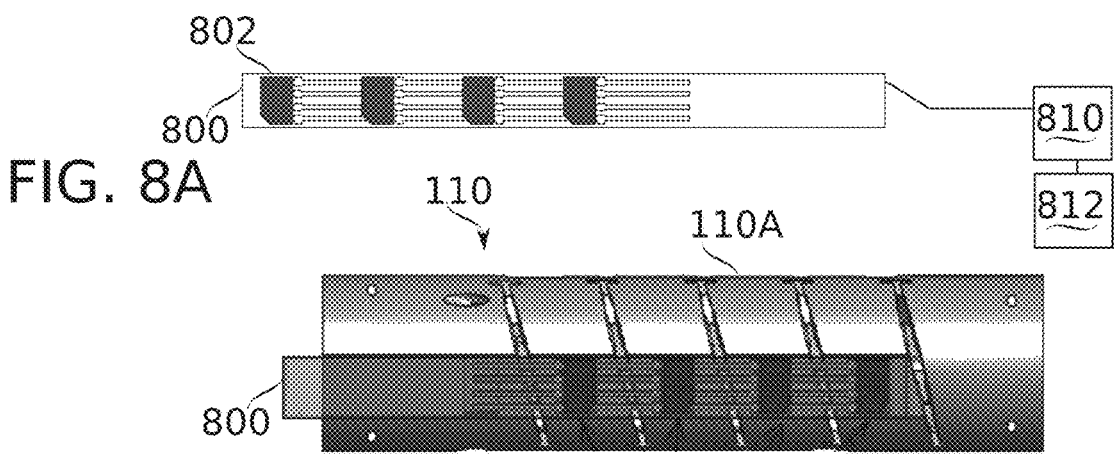
FIG. 8A
FIG. 8B
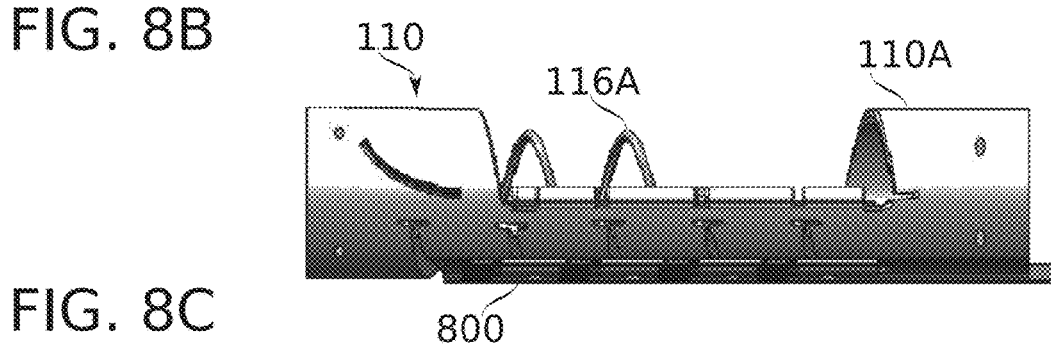
FIG. 8C

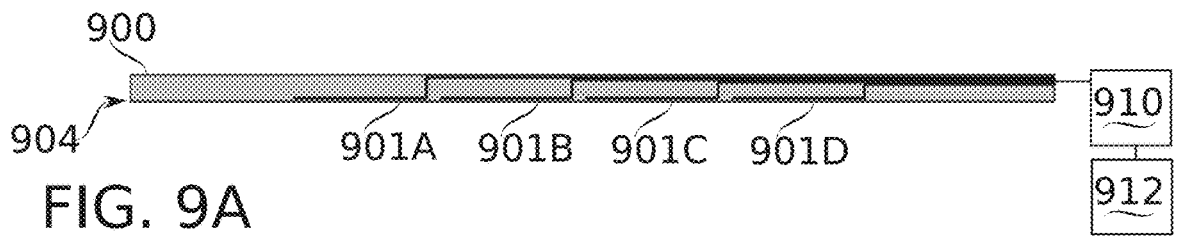
FIG. 9A
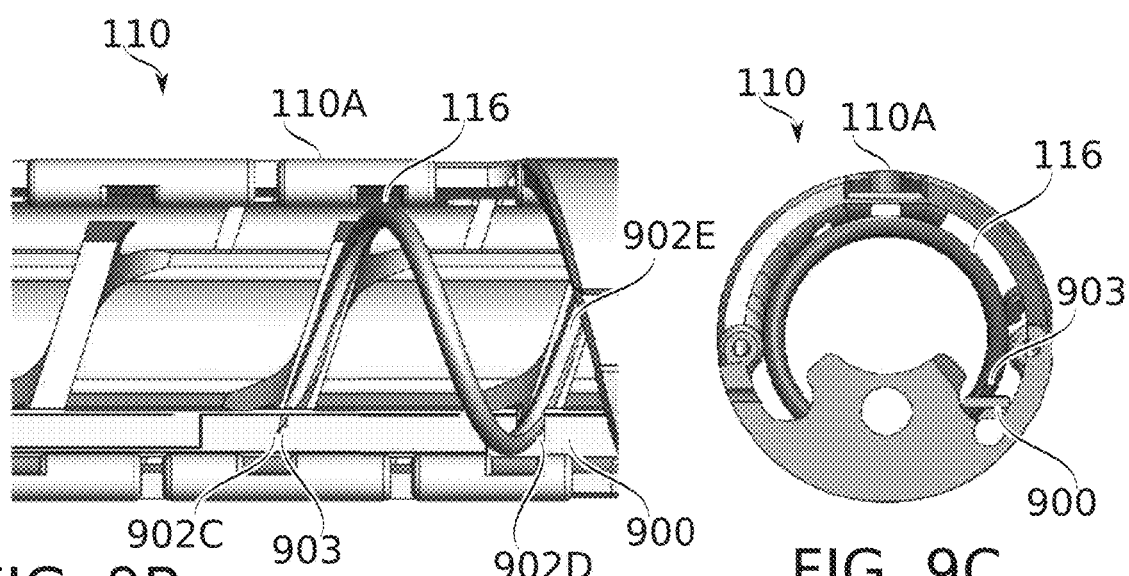
FIG. 9B
FIG. 9C
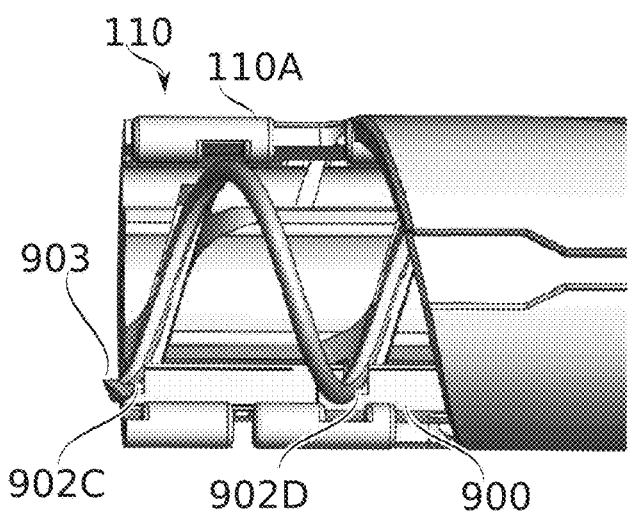
FIG. 9D

SUTURING WITH AN ENDOLUMINAL GASTROPLASTY DEVICE

RELATED APPLICATIONS

This application is a National Phase of PCT Patent Application No. PCT/IL2021/050208 having International filing date of Feb. 23, 2021, which claims the benefit of priority under 35 USC § 119 (e) of U.S. Provisional Patent Application No. 62/981,573 filed on Feb. 26, 2020. The contents of the above applications are all incorporated by reference as if fully set forth herein in their entirety.

FIELD AND BACKGROUND OF THE INVENTION

The present invention, in some embodiments thereof, relates to the field of bariatric surgery; and more particularly, to endoluminal placement of gastric sutures.

Obesity and related pathologies such as type 2 diabetes are of growing concern worldwide. Gastrointestinal weight-loss surgery (bariatric surgery) has been shown to be effective in achieving sustained weight loss and amelioration of type 2 diabetes. Gastric volume reductions via open surgical- or laparoscopic sleeve-gastrectomy have proven to be one of the most effective forms of treatment.

Surgical procedures are not without risks. Complications such as procedure-related leak, severity of co-morbidities, and surgeon learning curve are but a few of the factors that have been, and will be, limiting extensive adoption of this approach.

In addition to being a relatively non-invasive form of gastric volume reduction procedure, endoluminal gastric sleeve formation carries the potential for reduced risk of leakage from the stomach. Because the stomach itself is optionally left intact, another potential advantage of an endoluminal technique over sleeve formation by surgical resection is reversibility, for example, in case of complications.

SUMMARY OF THE INVENTION

According to an aspect of some embodiments of the present disclosure, there is provided a bougie configured for placing suturing in a body cavity wall, the bougie including: a vacuum clamping domain, sized for insertion into the body cavity, and including surfaces defining an interior space, and apertures into the interior space configured to receive tissue of the body cavity wall upon application of suction thereto; a needle within the interior space, with suture attached to the needle; and a suture clip within the interior space; wherein the needle is actuatable to translate along a path within the interior space while carrying the suture through the tissue; and wherein the suture clip is positioned to capture the suture at a position along the path, and operable to clamp the captured suture.

According to some embodiments of the present disclosure, the suture clip includes a suture-catching aperture, and the predetermined path extends through the suture-catching aperture.

According to some embodiments of the present disclosure, the needle includes a helical needle, the predetermined path includes a helical path along which the helical needle translates by rotation, and the suture clip is positioned along the helical path.

According to some embodiments of the present disclosure, a suture catching portion of the suture clip is configured so that after capture of the suture, the suture remains free to loosely translate longitudinally past the suture clip.

According to some embodiments of the present disclosure, the suture clip includes a plurality of clamping portions, and the suture is clamped by movement of the clamping portions closer to one another.

According to some embodiments of the present disclosure, the clamping portions are configured to insert one inside the other, and the clamping motion includes inserting one clamping portion inside the other.

According to some embodiments of the present disclosure, the clamping movement includes rotating one of the plurality of clamping portions with respect to the other.

According to some embodiments of the present disclosure, the rotating includes moving apertures of the plurality of clamping portions out of alignment with each other.

According to some embodiments of the present disclosure, the bougie includes a suture tightener at least partially within the interior space, also positioned to capture the suture at a position along the path, and operable, from outside the bougie, to move to apply a pulling force on the suture to reduce a length of the tissue-engaged suture.

According to some embodiments of the present disclosure, the bougie includes a plurality of sensing positions, positioned along the path, each sensing position configured with a sensor configured to sense the adjacent presence of the needle.

According to an aspect of some embodiments of the present disclosure, there is provided a bougie configured for placing suturing in a body cavity wall, the bougie including: a vacuum clamping domain, sized for insertion into the body cavity, and including surfaces defining an interior space, and apertures into the interior space configured to receive tissue of the body cavity wall upon application of suction thereto; a needle within the interior space, with suture attached to the needle; and a suture tightener at least partially within the interior space; wherein the needle is actuatable to translate along a path within the interior space while carrying the suture through the tissue; and wherein the suture tightener is positioned to capture the suture at a position along the path, and operable, from outside the bougie, to move to apply a pulling force on the suture to reduce a length of the tissue-engaged suture.

According to some embodiments of the present disclosure, the captured suture slides freely with respect to the suture tightener while the suture tightener moves to reduce the length of tissue-engaged suture.

According to some embodiments of the present disclosure, the suture tightener, when moved to reduce the length of tissue-engaged suture, doubles over the suture so that both ends of the suture are on a same side of the suture tightener.

According to some embodiments of the present disclosure, the suture tightener includes a spindle over which the doubled-over suture slides.

According to some embodiments of the present disclosure, the spindle is narrower toward the middle than at the ends.

According to some embodiments of the present disclosure, the spindle is rotatably mounted to the suture tightener.

According to some embodiments of the present disclosure, the suture tightener includes an aperture positioned along the path, and the suture tightener captures the suture when the needle pulls the suture through the aperture.

According to an aspect of some embodiments of the present disclosure, there is provided a bougie configured for placing suturing in a body cavity wall, the bougie including: a vacuum clamping domain, sized for insertion into the body cavity, and including surfaces defining an interior space, and apertures into the interior space configured to receive tissue of the body cavity wall upon application of suction thereto; a needle within the interior space, with suture attached to the needle; wherein the needle is actuatable to translate along a path within the interior space while carrying the suture through the tissue; and a plurality of sensing positions, positioned along the path, each sensing position configured with a sensor configured to sense the adjacent presence of the needle.

According to some embodiments of the present disclosure, each sensing position has a separate respective sensor.

According to some embodiments of the present disclosure, the sensor includes a Hall effect sensor.

According to some embodiments of the present disclosure, the needle is magnetized.

According to some embodiments of the present disclosure, the sensor includes an electrical conductor.

According to some embodiments of the present disclosure, sensing includes detection of a break in the electrical conductor.

According to some embodiments of the present disclosure, the break detection includes sensing a change in impedance of the electrical conductor.

According to some embodiments of the present disclosure, the break detection includes sensing opening of an electrical circuit due to the break in the electrical conductor.

According to some embodiments of the present disclosure, the sensor senses electrical contact of the sensor with the needle.

According to some embodiments of the present disclosure, the plurality of sensing positions share a sensor.

According to some embodiments of the present disclosure, the sensor senses a cumulative number of the sensing positions adjacent to the needle.

According to some embodiments of the present disclosure, the sensor includes a tube extending between the sensing positions, and senses pressure within the tube.

According to some embodiments of the present disclosure, the needle includes a helical needle, the path includes a helical path along which the helical needle translates by rotation, and the plurality of sensing positions are also arranged along a longitudinal axis of the vacuum clamping domain.

According to some embodiments of the present disclosure, the bougie includes a needle position indicator, configured to indicate the position of the needle based on the presence of a portion of the needle adjacent to each of the plurality of sensing positions.

According to some embodiments of the present disclosure, the needle position indicator is configured to indicate the position of the needle in steps corresponding to the adjacent presence or adjacent absence of the needle.

According to some embodiments of the present disclosure, the bougie includes a needle position indicator configured to indicate signals produced by fluctuations in the interaction of the needle with the plurality of sensing positions, smaller than fluctuations indicating a difference between presence and absence of the needle at the sensing positions.

According to some embodiments of the present disclosure, the bougie includes a suture clip positioned within the interior space and configured to capture the suture at a position along the path, and operable to clamp the captured suture.

According to some embodiments of the present disclosure, the bougie includes a suture tightener at least partially within the interior space, positioned to capture the suture at a position along the path, and operable, from outside the bougie, to move to apply a pulling force on the suture to reduce a length of the tissue-engaged suture.

According to an aspect of some embodiments of the present disclosure, there is provided a method of securing a suture placed within a body cavity wall, the method including: translating a needle through tissue along a predetermined path within an interior space of a bougie; translating the needle through and/or alongside a suture catching portion of a suture clip pre-positioned within the interior space along the predetermined path; translating the needle past the suture catching portion, bringing a portion of the suture to a capturing zone of the suture clip defined by the suture catching portion; and actuating the suture clip to clamp the portion of the suture.

According to some embodiments of the present disclosure, the predetermined path is a helical path, and the needle is a helical needle.

According to some embodiments of the present disclosure, the method includes releasing the suture clip from the interior space.

According to some embodiments of the present disclosure, suture catching portion includes an aperture through which the predetermined path extends.

According to some embodiments of the present disclosure, the method includes translating the needle further along the predetermined path to bring the suture to a capturing portion of a suture tightener; and, before the actuating, operating the suture tightener to reduce a length of the suture engaged with tissue.

According to an aspect of some embodiments of the present disclosure, there is provided a method of monitoring the placement of suture within a body cavity wall, the method including: translating a needle through tissue along a predetermined path within an interior space of a bougie; sensing, at each a plurality of sensing positions positioned along the path, presence of the needle at the respective sensing position; and indicating the needle position, based on the sensing.

According to some embodiments of the present disclosure, the sensing includes mechanically breaking an element at least one of the plurality of sensing positions.

According to some embodiments of the present disclosure, the sensing includes detection of a pressure change induced in a tube by movement of the needle against the tube.

According to some embodiments of the present disclosure, the sensing includes detection of a magnetic field change.

According to some embodiments of the present disclosure, the sensing includes detection of an electrical contact between the needle and an electrical conductor positioned at one or more of the plurality of sensing positions.

Unless otherwise defined, all technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced.

In the drawings:

FIGS. 1A-1B schematically represent a bougie configured for shaping and intra-cavity suturing of tissue of a body cavity, according to some embodiments of the present disclosure;

FIGS. 1J-1M illustrate alternative methods of threading a suture clip, according to some embodiments of the present disclosure;

FIGS. 6A-6D schematically represent a suture clip which clips by a rotational movement, according to some embodiments of the present disclosure;

FIGS. 7A-7D schematically represent a pressure sensor arrangement for measuring movements and/or positioning of a needle, according to some embodiments of the present disclosure;

FIGS. 8A-8C schematically represent a magnetic sensor arrangement for measuring movements and/or positioning of a needle, according to some embodiments of the present disclosure;

FIGS. 9A-9D schematically represent a circuit board-based sensor arrangement for measuring movements and/or positioning of a needle, according to some embodiments of the present disclosure;

DESCRIPTION OF SPECIFIC EMBODIMENTS OF THE INVENTION

Figure 1C:
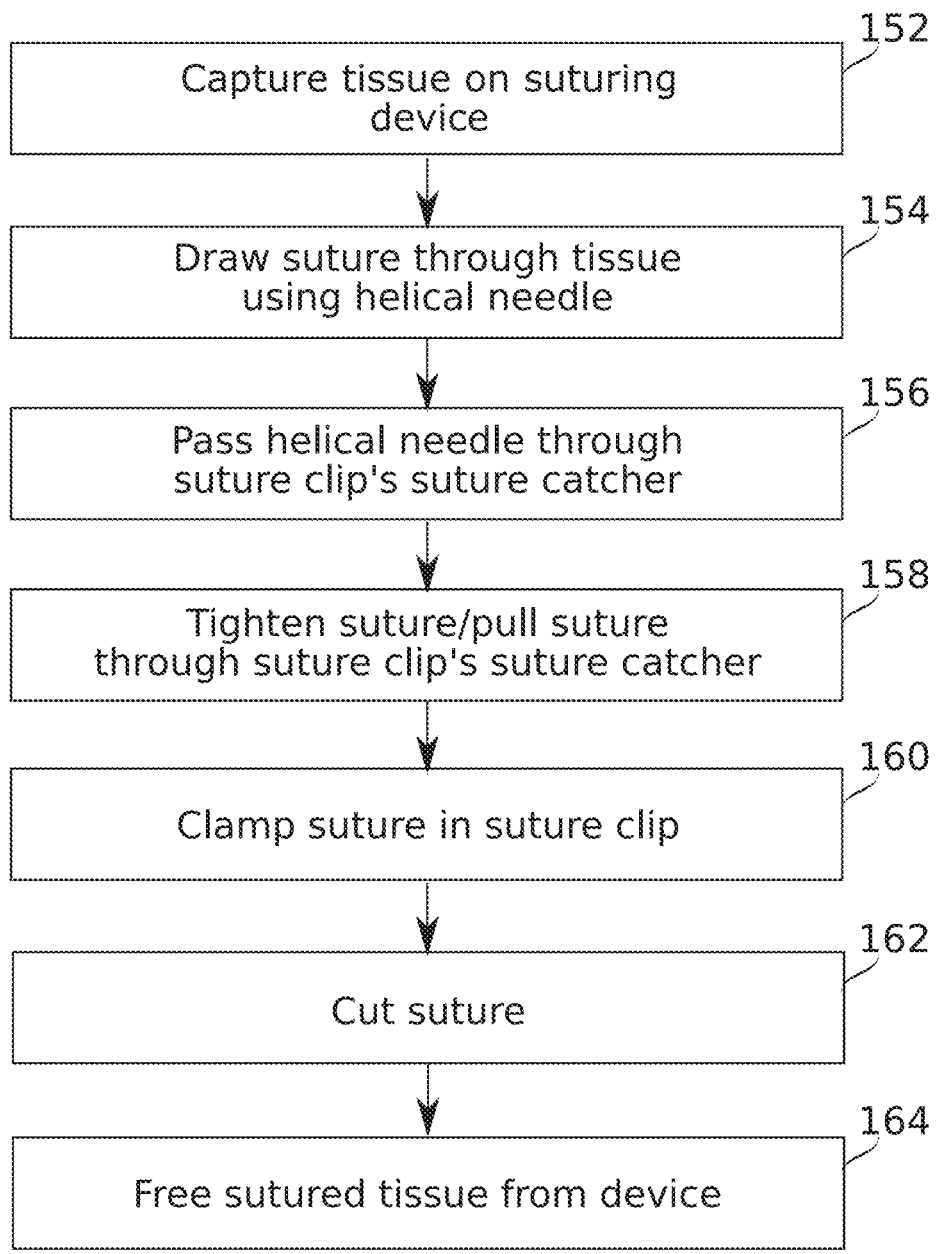
FIG. 1C is schematic flowchart of a method of suturing from within a tissue securing device, according to some embodiments of the present disclosure.

The present invention, in some embodiments thereof, relates to the field of bariatric surgery; and more particularly, to endoluminal placement of gastric sutures.

Overview

An aspect of some embodiments of the present disclosure relates to suture clips configured to be placed in a predetermined path of a suturing needle advancing through a device inserted to a body cavity, and remotely operated from that position to secure and clamp suturing.

The suture clip, in some embodiments, is initially placed at its position within a suturing bougie used for device-guided suturing of tissue from within a body cavity, such a stomach. More particularly, in some embodiments, the suturing bougie allows placement of a plurality of stitches in tissue of the body cavity, using a needle moving through an interior space defined by the suturing bougie, and at least partially longitudinally along the bougie. Tissue enters the bougie, for example, under suction. Optionally, the tissue is supported to obtain a particular pattern and/or depth of suturing by surfaces of the bougie arranged (for example, by a pattern of apertures or "fenestrations") to allow some tissue portions to enter the interior space, while holding adjacent tissue portions outside it.

The predetermined path, in some embodiments, is a path defined by mechanical arrangements within the interior space to guide a needle therethrough. The combined configuration of the held tissue and the predetermined path of the suturing needle through the suturing bougie determines a resulting pattern of suture stitches.

In some embodiments, the suturing needle is helical, and advances by helical rotation along a helical path. The needle may be driven by a needle drive comprising, for example, a cable, screw, ratchet, and/or other mechanism. Optionally, the needle is another shape—for example, straight or curved-planar—and moves along a path of a different shape, e.g., a straight path, a combination of straight and curved-planar paths, or another arrangement.

A device-integrated suturing clip, used with such a suturing needle configuration, encounters potential problems for reliably capturing the suture, for remote manipulation to clamp onto the suture, and for ensuring that the clip clamps at a position near to the point where the suture exits tissue that it is engaged with to create stitches.

In some embodiments, the suture clip is initially positioned along a predetermined path of the needle, so that the needle passes through a loop and/or aperture of the suture clip. This allows the suture clip to dependably capture the suture (that is, the suture is threaded through the loop and/or aperture). In some embodiments, the needle passes through or alongside a partially open-sided structure which captures the suture, for example, an arrangement of oppositely positioned hooks. The capturing comprises ensuring that some portion of the suture remains (or reliably returns to) a predetermined zone upon which the suturing clamp is later actuated to clamp down, while the suture also remain free to slide longitudinally through that zone, for example as the needle continues to move forward, and/or the suture is pulled on to tighten it. The suture clip is preferably positioned so that the clamping zone is close to the place where the needle exits tissue after forming a stitch. This helps to ensure (at least, once the suture is suitably tightened) that the suture clip is positioned close enough to the end of the stitching and/or plications of the tissue lumenal wall so that the suture stitches themselves remain tight.

In embodiments threading the suture through a loop and/or aperture, then the predetermined zone optionally comprises the confines of that loop or aperture. It is a potential advantage for the predetermined zone to be relatively small, for example, since this allows the clip to be smaller and/or operable to clamp from its original mounting position. Clamping is performed, for example, by constraining the loop/aperture area still further, e.g., adjusting a shape of the loop/aperture, by pressing another element into the loop/aperture, or another method. Optionally, clamping comprises contorting the suture, e.g., so that it bends at least one time away from a direction in which force is transmitted to the suture at the point where it enters the clamp.

In some embodiments, the suturing clip comprises a plurality of pieces, one of which is actuatable to fittingly insert into another piece, thereby pressing the suture (which threads one of the pieces) between walls of the two pieces. Additionally or alternatively, in some embodiments, the suturing clip comprises a plurality of pieces, one of which is actuatable to rotate relative to another piece, thereby contorting the suture into a shape which resists pulling.

Clamping is preferably performed while the suturing clip remains within the bougie, e.g., near to the site where suturing finishes (that is, where the needle exits the last suturing hole it makes in the tissue). One or more clips are optionally placed between sutures, e.g., to allow sutures to be clipped off individually and/or in smaller groups.

To achieve actuation remotely, in some embodiments, at least one of the suturing clip pieces is moved by a control member, e.g., by pulling on a wire, string, rod, and/or cable; rotating a socketed and/or threaded element; or another mechanism.

An aspect of some embodiments of the present disclosure relates to suture tightening devices configured to be placed in a predetermined path of a suturing needle advancing through a suturing device (e.g., a bougie) inserted to a body cavity, and remotely operated, once suture is captured, to pull on and shorten a length of suture engaged in a sutured region of tissue (tissue-engaged suture). The tightening is performed, for example, in preparation for applying a suture clip to the suture.

In some embodiments, the suture tightening device captures the suture loosely, so that the suture continues to slide freely through the suturing device while the suture tightening device pulls on and shortens the length of tissue-engaged suture. Free movement of the suture relative to the suture tightening device provides a potential advantage, by allowing the needle-attached end of the suture to remain stationary (and still attached to the needle) once the needle has finished its track.

In ordinary hand suturing, the suture needle itself is a type of "suture tightening device"—pulling on it tightens the stitches it makes (by shortening the length of tissue-engaged suture). However, mechanically driven suturing, for example using a helical needle, introduces problems for which a separate suture tightening device provides potential solutions.

A helical needle is potentially well suited to creating suture stitches e.g., insofar as its combined longitudinal and rotational path of movement passes both horizontally (due to rotation) through one or more tissue thicknesses, and longitudinally to repeat such passes. However, once the suture stitches are placed (that is, once the suture is fully engaged with tissue), it is potentially preferable to be able to tighten the stitches by simple pulling, without the complication of generating helical motion. In some embodiments, a suture tightener provides control, separate from the needle control, which allows tightening using a non-helical motion.

Compared, e.g., to a solution that transfers a helical needle from a helical driving mechanism to use with a pulling-only driving mechanism, a separate suture tightening device provides the potential advantage that the relatively cumbersome helical needle itself does not need to be navigated through the confined spaces of the bougie. The suture tightening device only needs to move the suture itself. Optionally, it is more compact than the helical needle.

In some embodiments, the suture tightening device doubles over the suture as it moves (e.g., is pulled proximally) so that both ends of the suture (e.g., a tissue-attached end and a needle-attached end) are on a same (e.g., distal) side of the suture tightening device. This is a potential advantage for shortening the tightening distance needed for the device, e.g., so that a 1 cm movement of the suture tightening device produces about a 2 cm shortening of the tissue-engaged length of suture.

In some embodiments, the suture tightening device comprises a spindle (e.g., mounted to a harness) which is shaped (e.g., flared toward the sides) so that tension on a suture line looped over the spindle tends to pull the suture toward a middle region of the spindle. This is a potential advantage for controlling the position of the suture, and/or keeping it away from sharp and/or pinching corners and crevices. In some embodiments, the spindle rotates freely (e.g., is rotatably mounted to the harness), assisting in the free motion of the suture. In some embodiments, a capturing aperture of the suture tightening device is defined at least in part by the spindle, and optionally also by a harness holding the spindle.

In some embodiments, a suturing clip and suture tightening device are arranged so that suture position relative to the suturing clip is controlled by movement of the suture tightening device, e.g., to a predetermined location. For example, the suture tightening device, as it is pulled, optionally enters a channel sized and positioned so that the portion of the suture extending directly from the suture tightening device to the location from which it exits tissue is forced to pass through the clamping zone of the suturing clip. For example, the suture is constrained to tighten against a member of the suturing clip which is involved in clamping. In such embodiments, the suturing clip need not itself comprise a loop or aperture, since capturing is managed by movement of the suture tightening device.

An aspect of some embodiments of the present disclosure relates to sensing of the position of a needle using sensors placed along a predetermined path of a suturing needle advancing through a device inserted to a body cavity.

In some embodiments, the sensors comprise a plurality of sensing sites, configured to sense and indicate the presence/absence of a needle portion at the site. In some embodiments, a plurality of sensors are placed at an interval shorter than a longitudinal length of the needle. In some embodiments, the needle is a helical needle, and the sensors are placed at intervals about the size of the longitudinal distance spanned by one helical turn of the needle, and/or a multiple thereof.

Optionally, the sensors sense needle presence/absence by a change in pressure (e.g., pressure on a tubular member), by magnetic field changes (e.g., using a Hall effect sensor), and/or by changes in electrical conductivity through the sensor (e.g., by breaking elements of the sensor, and/or by making new electrical contacts through the sensor).

In some embodiments, the position sensing is converted to indications of needle position, based on steps defined by presence/absence of the needle next to each individual sensing position. Additionally or alternatively, in some embodiments, the position sensing data is used to indicate information about needle state and/or position smaller than a step, for example by showing indications of sensor fluctuations, e.g., in response to needle movement commands.

Before explaining at least one embodiment of the present disclosure in detail, it is to be understood that the present disclosure is not necessarily limited in its application to the details of construction and the arrangement of the components and/or methods set forth in the following description and/or illustrated in the drawings. Features described in the current disclosure, including features of the invention, are capable of other embodiments or of being practiced or carried out in various ways.

Exemplary Suture Clips

Reference is now made to FIGS. 1A-1B, which schematically represent a bougie 100 configured for shaping and intra-cavity suturing of tissue of a body cavity, according to some embodiments of the present disclosure.

Three main sections of bougie 100 are represented as bougie capsule section 101 (distally), bougie main body 102, and bougie control handle 103 (proximally).

Bougie capsule section 101 (herein, a bougie capsule section is also referred to herein as a "capsule"), in some embodiments, comprises a suction clamping domain 110, which in turn comprises one or more fenestrations 111, configured to receive tissue from the body cavity under suction, and to hold and/or position it in preparation for one or more surgical modifications such as suturing. Suction clamping domain 110, in some embodiments, comprises supporting surfaces onto which tissue collapses when suction is applied to the device in use. The supporting surfaces comprise a body 110A of the clamping domain 110 (formed, e.g., as a partial tube and/or spine), and/or other features along clamping domain 110 such as aperture shaping elements, optionally including longitudinal blocker 115, and/or lateral blockers 117. Within the supporting surfaces is defined a space (also referred to herein as a cavity) which receives and positions tissue under suction, and within which said space suturing is performed upon the positioned tissue.

During suturing, in some embodiments, a helical needle moves in a likewise helical motion along the space, suturing the positioned tissue by passing alternately, as it advances, through a first tissue portion tissue collapsed into the space from one side of the body cavity, and then through a second tissue portion from the other side of the body cavity, also collapsed into the space alongside the first tissue portion.

Herein, fenestrations 111 are moreover part of the aperture region of a bougie capsule section 101. Fenestrations 111, in some embodiments, are configured to be changed in size, shape, and/or topology by actuation of one or more aperture shaping elements. Such fenestrations are also referred to herein as "dynamic" fenestrations.

Aperture shaping element actuation and concomitant changes in dynamic fenestrations 111 is used, in some embodiments, to control one or more aspects of lumen tissue attachment, lumen tissue positioning, or lumen tissue suction depth (e.g., in preparation for suturing); or of tissue release. In some embodiments, tissue release includes release of suturing or other surgical material which may be attached (e.g., sewn, clipped, and/or stapled) to the lumen tissue while it is engaged with the bougie capsule section 101.

Examples of aperture shaping elements, in some embodiments, include a longitudinal blocker 115, and/or lateral blockers 117.

A longitudinal blocker 115, in some embodiments, comprises an element such as a stiffened strip or rod that longitudinally spans at least a portion of suction clamping domain 110, substantially dividing it into two sides of fenestrations 111 which extend longitudinally alongside one another. Longitudinal blocker 115 is optionally removable, re-joining the divided fenestrations 111. This is a potential advantage in tissue and/or suture release; for example to release of the suction clamping domain 110 from suturing which crosses between two body cavity lumen tissue portions (i.e., the first and second tissue portions mentioned hereinabove), and on an internal side of the longitudinal blocker 115 (that is, within the internal space of the suction clamping domain 110).

Lateral blockers 117, in some embodiments, comprise one or more elements, such as lengths of cord, which cross laterally across suction clamping domain 110 (optionally directly laterally, or diagonally). A crossing element creates a division of the suction clamping domain that separates different fenestrations 111 on either side of the element. Lateral blockers 117, in some embodiments, are releasable and/or removable to remove the separation.

Examples of longitudinal blocker 115 and lateral blockers 117 are described, for example, in International Patent Publication No. WO 2016/056016, the contents of which are included by reference in their entirety.

In some embodiments, a distal tip 112 of bougie capsule section 101 is provided. Distal tip 112 is optionally transparent, and/or terminates in an aperture large enough (for example, about 6-8 mm in diameter) to pass the distal end of an endoscope probe or other tool out of.

Bougie main body 102, in some embodiments, comprises a tube 121, along which one or more longitudinally extended control members 120 pass, externally and/or internally. In some embodiments, control members 120 interconnect between actuatable elements of the bougie capsule section 101 (e.g., longitudinal blocker 115 and/or lateral blocker 117), and the bougie control handle 103 (e.g., control knobs 122). In some embodiments, tube 121 has an inner diameter large enough (for example, about 6-10 mm) to insert an endoscope probe or other tool through.

Any control member 120, control knob 122 or other control device is optionally provided with an encoder 121A which senses operation of the control member. Data from the encoder 121A, in some embodiments, is used to determine an operating state of the bougie 100. In some embodiments, skew between movement measured by encoder 121A and sensed results (e.g., within the bougie capsule section 101) is monitored. Optionally, the occurrence of measured skew is treated as an indication that there is mechanical resistance, and this is furthermore indicated to the operator, e.g., by means of logic circuitry and one or more indicators on the bougie 100 itself, or connected to the bougie 100.

Distal tip 112 is preferably provided with a tapered shape to assist in insertion of bougie 100 along a natural body passage such as an esophagus. Bougie capsule section 101 and bougie main body 102 are preferably sized (in diameter and length) and shaped (at least in an insertion configuration) to allow insertion along a natural body passage such as an esophagus to reach a target organ such as a stomach.

Bougie control handle 103, in some embodiments, comprises one or more control knobs 122, configured to control manipulation of control members 120. Optionally, one or more ports 124 are provided, sized to allow insertion of an endoscope or other tool, for passage along the lumen of tube 121 into bougie capsule section 101, and optionally to and/or out of distal tip 112.

Reference is now made to FIG. 1C, which is schematic flowchart of a method of suturing from within a tissue securing device, according to some embodiments of the present disclosure. Reference is also made to FIG. 1D-1I, which schematically illustrate stages in the method of suturing of FIG. 1C, according to some embodiments of the present disclosure. Further reference is made to FIGS. 1J-1M, which illustrate alternative methods of threading a suture clip, according to some embodiments of the present disclosure. Additional reference is made to FIG. 12, which illustrates a block diagram of a suturing subsystem 1200 comprising a needle 116 and suturing clip 130, according to some embodiments of the present disclosure.

Figure 1D:
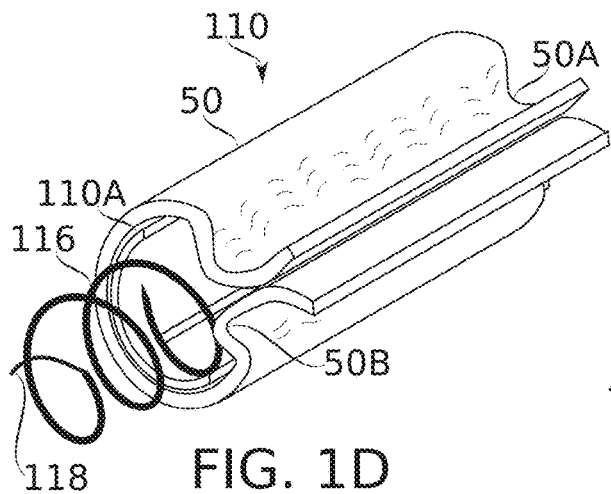
FIGS. 1D-1I schematically illustrate stages in the method of suturing of FIG. 1C, according to some embodiments of the present disclosure.
Figure 1E:
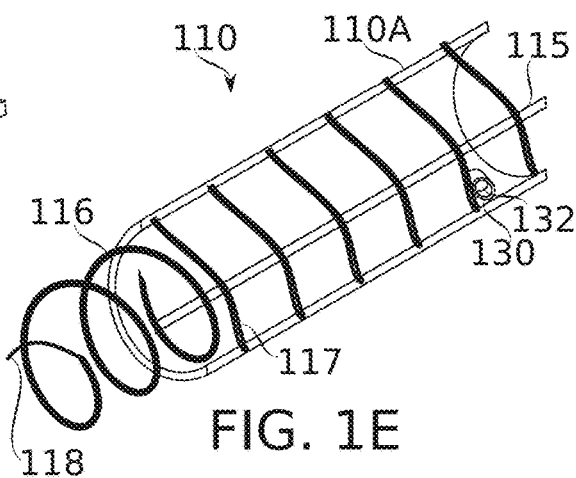
Figure 1F:
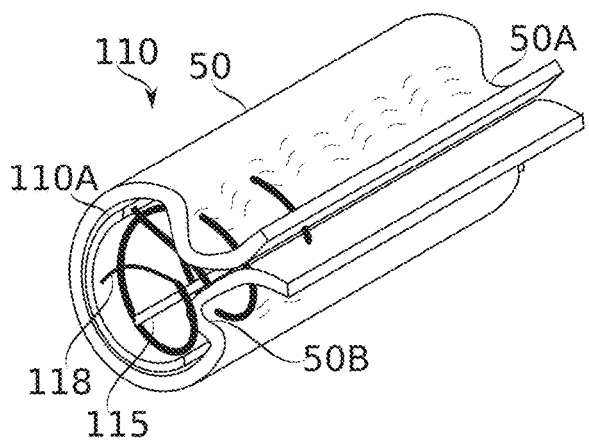

At block 152 of FIG. 1C, in some embodiments, tissue is captured on a suturing device, for example, by vacuum forming of stomach tissue 50 around a vacuum clamping domain 110 of a capsule 101 of a bougie 100, supported by surfaces of body 110A and by blockers 115, 117. This situation corresponds, in some embodiments, to what is shown in FIG. 1D (optionally without needle 116 yet having been advanced to the position shown). A first portion 50A of stomach tissue 50 is vacuum clamped along one side of the fenestrations defined by blockers 115, 117, and a second portion 50B of stomach tissue 50 is vacuum clamped along the other side (i.e., on either side of longitudinal blocker 115). Needle 116 is attached to suture 118, and pulls suture 118 along as it is advanced. FIG. 1E shows a bougie 100 as it would appear in FIG. 1D without the stomach tissue 50 formed around it, revealing more of the underlying detail.

Figure 1G:
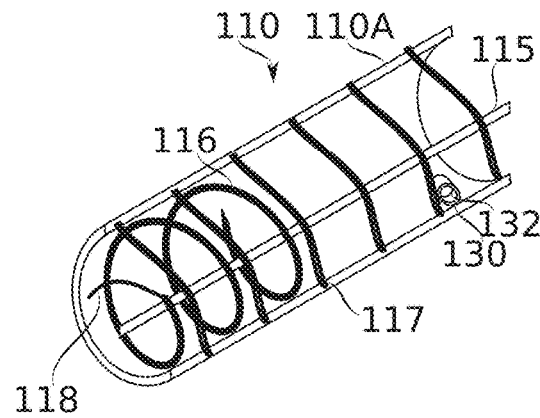
Figure 1H:
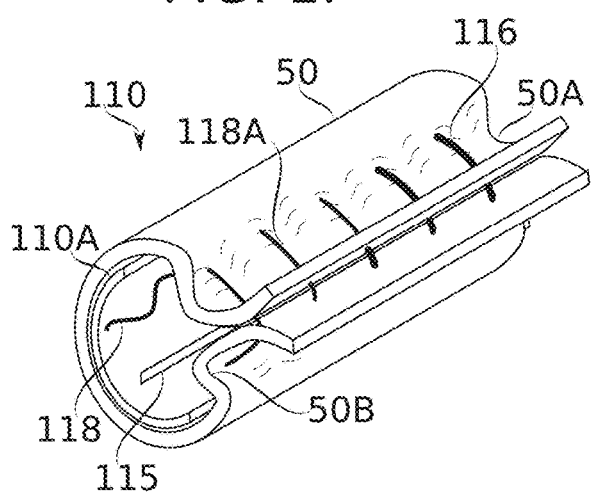
Figure 12:
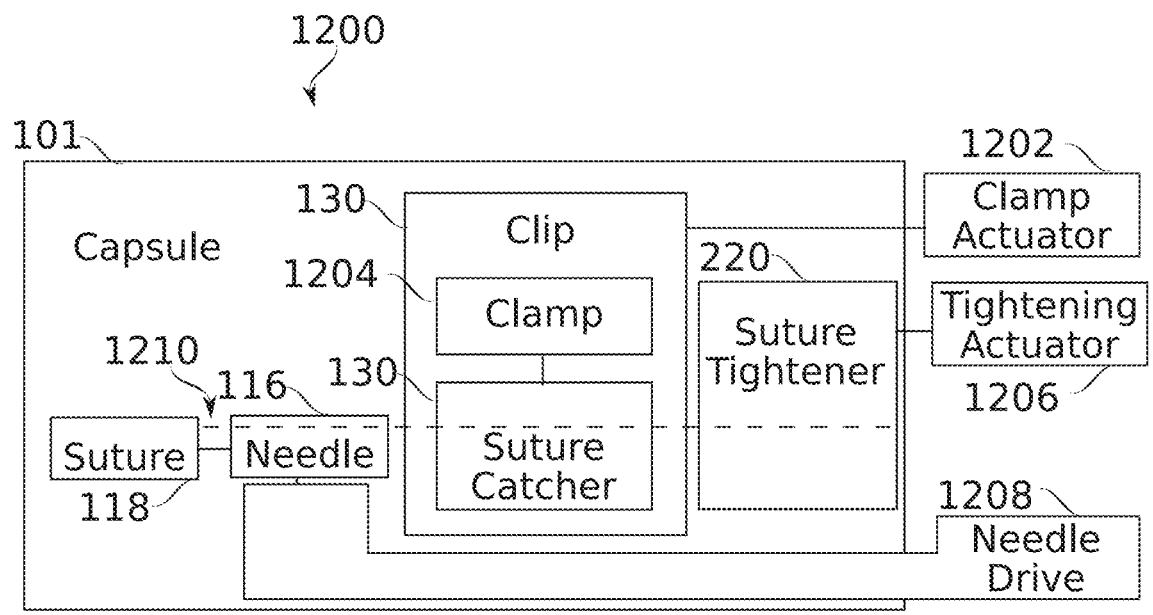
FIG. 12 illustrates a block diagram of a suturing subsystem comprising a needle and suturing clip, according to some embodiments of the present disclosure.

At block 154, in some embodiments, suture 118 is drawn through tissue 118 by advancing needle 116 in a helical motion. This corresponds, in some embodiments, to the situation of FIGS. 1F-1G (FIG. 1G is a version of FIG. 1F with the appearance of stomach tissue 50 suppressed). In some embodiments, needle 116 is advanced along a path 1210 using a needle drive 1208 (FIG. 12). Needle drive 1208 optionally comprises, for example, cabling and/or gearing which impinge upon needle 116 and cause needle 116 to advance by corkscrew rotation when actuated (e.g., actuated by rotation and/or pulling).

Figure 1I:
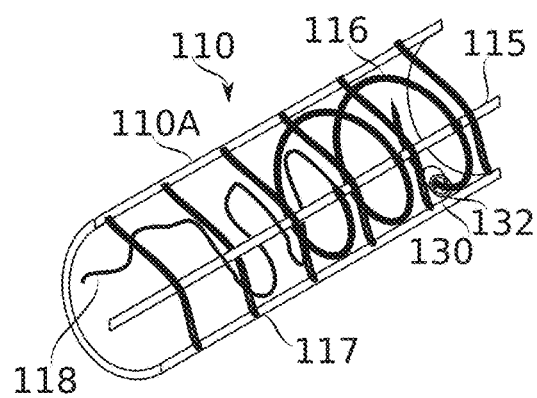

At block 156, in some embodiments, helical needle 116 is passed through and/or against a suture catcher 132 of suture clip 130. This corresponds, in some embodiments, to the situation of FIGS. 1H-1I (FIG. 1I is a version of FIG. 1H with the appearance of stomach tissue 50 suppressed). It is a potential advantage to mount suture clip 130 close to (e.g., within 10 mm or less) the needle exit of the last stitch. This potentially reduces slack in the suture line.

A suture catcher 132, in some embodiments, comprises a portion of suture clip 130 through and/or against which a portion of suture 118 is reliably passed/pressed upon sufficient advancement of needle 116. A suture catcher 132 is optionally of a loop configuration, circumferentially closed to define an aperture, which suture 118 enters by passing through an aperture of the loop. Alternatively, suture catcher 132 comprises an open-sided configuration, which allows suture 118 to enter it (e.g., across a lateral opening of the suture catcher), optionally even after the needle has passed it by.

A loop configuration has the potential advantage of capturing suture 118 as a consequence of passing needle 116 through the loop (i.e., threading of the suture through the loop), without leaving an exit allowing lateral suture escape, and while suture 118 remains loosely held. Furthermore, to obtain this capture, there is no requirement for actuation of the suture catcher 132. Since suture 118 is only loosely held initially, it can be tightened later in the procedure, optionally without significant interference from clip friction. More particular embodiments of loop-type suture catchers 133, 131 are shown with suture clips 130A, 130B in FIGS. 1J-1M, as further described hereinbelow.

An open sided loop catcher configuration has the potential advantage of merely requiring the suture 118 to pass alongside (and not through) it; allowing it, for example, to be brought in from the side after needle 116 has passed. Such a configuration is furthermore compatible, for example, with implementation as a pair of clamping jaws. However, an open-sided configuration is associated with a potential risk of the suture 118 escaping the suture catcher 132 before clamping is actuated. If a separate retaining mechanism is also provided to prevent such escape, then this may itself interfere with suture release later on and/or add complexity to the device. If clamping by suture catcher 132 is at least partially actuated immediately upon passage of needle 116 (e.g., by return of a spring displaced by passage of needle 116), this may reduce a chance for suture 118 to escape, but the suture clip 130 may itself interfere with tightening of the suture.

FIGS. 1J-1K (FIG. 1K is a magnified section of FIG. 1J) illustrate a clip 130A with an aperture 133 defined by a loop-type catcher configured as a cylinder 134. Clamping (e.g., as described in relation to block 160) optionally comprises inserting a matching plug into the cylinder 134, for example as described in relation to FIGS. 3C and/or 4A-4D.

FIGS. 1L-1M (FIG. 1M is a magnified section of FIG. 1L) illustrate a clip 130B with an aperture defined by a loop-type catcher configured as a protruding loop 131. Clamping (e.g., as described in relation to block 160) optionally comprises withdrawing loop 134 into clip body 132, which comprises tight confines which press on loop 134 and/or captured suture 118.

At block 158, in some embodiments, suture 118 is tightened. This comprises pulling on suture 118 so that the portion of it engaged within stitching length 118A of suture 118 tightens (and, effectively, shortens, as more of suture 118 is pulled longitudinally out of the region of suture 118 engagement with tissue 50). In some embodiments, tightening suture 118 is performed using a secondary tightening mechanism (optional suture tightener 220, which is optionally actuated by tightening actuator 1206), for example as described in relation to FIGS. 3A-3B and/or 5A-5D, herein.

At block 160, in some embodiments, suture clip 130 is clamped. Clamping is optionally implemented mechanically in different ways. Principles of mechanism clamping used in some embodiments of the present disclosure include pressing suture 116 between surfaces to create friction, and bending clamping suture 116 to interfere with the direct transmission of pulling forces exerted on it. In some embodiments, suture clip 130 is configured so that holding power exerted through one or both of these principles is itself enhanced by pulling on the suture. Examples of suture clamping mechanisms functioning as a clamp 1204 (FIG. 12) are described, for example, in relation to FIGS. 3C and 4A-4D; and FIGS. 6A-6D.

A clamping actuator 1202 is optionally implemented mechanically in different ways in different embodiments. For example, in some embodiments, suture clip 130 comprises a plurality of parts which are moved closer to one another (e.g., closing against each other and/or inserting one inside the other) by actuation of a control member 120 (e.g., a wire or string which receives longitudinal tension from a control side of the bougie which remains outside the body cavity). Additionally or alternatively, in some embodiments, suture clip 130 comprises a plurality of parts which rotate with respect to each other, e.g., as socket and screw and/or around an axle. The rotation is optionally actuated using a control member 120 which is rotated or receives longitudinal tension from a control side of the bougie.

At block 162, in some embodiments, suture 118 is cut. In some embodiments, a cutting edge is provided as part of bougie 100 (e.g., within the internal space of the suction clamping domain 110, or another internal space of the bougie 110). Optionally, clip 130 itself comprises a cutting edge.

At block 164, in some embodiments, the sutured tissue is freed from the bougie 100. In some embodiments, this comprises releasing suction, removing longitudinal blocker 115 (e.g., by extracting it longitudinally), and removing lateral blockers 117 (e.g., by releasing them from one side, and optionally by pulling them lose by pulling back from the other side).

While embodiments described herein relate to a helical needle 116, it should be understood that the needle is optionally another shape, for example, a straight or curved needle. The clip suture catcher is pre-positioned within an interior space of the bougie where it receives the suture upon translation of the straight or curved needle through it (e.g., for a loop-type suture catcher) and/or alongside it (e.g., for an open-sided suture catcher).

Reference is now made to FIG. 2A-2D, which schematically represent stages in advancing of a needle 116 along a suction clamping domain 110 to enter and pass through a suture clip body 204, according to some embodiments of the present disclosure.

Figure 2A:
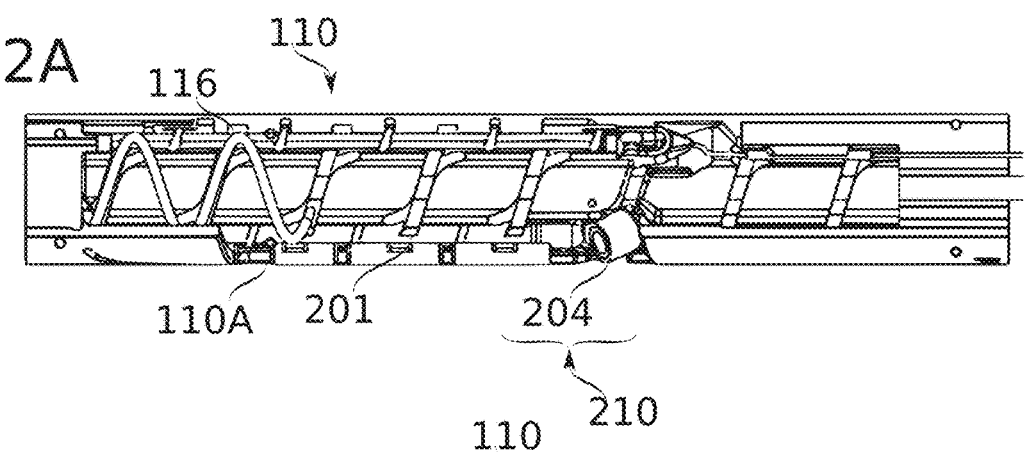
FIGS. 2A-2D schematically represent stages in advancing of a needle along a suction clamping domain to enter and pass through a suture clip body, according to some embodiments of the present disclosure.

In FIG. 2A, needle 116 is shown near the beginning of its longitudinal movement along suction clamping domain 110. In some embodiments, needle 116 is helical. Optionally, advancing of needle 116 is guided by needle guide tracks 201, which are spaced and pitched to match a helical pitch of needle 116.

Figure 2B:
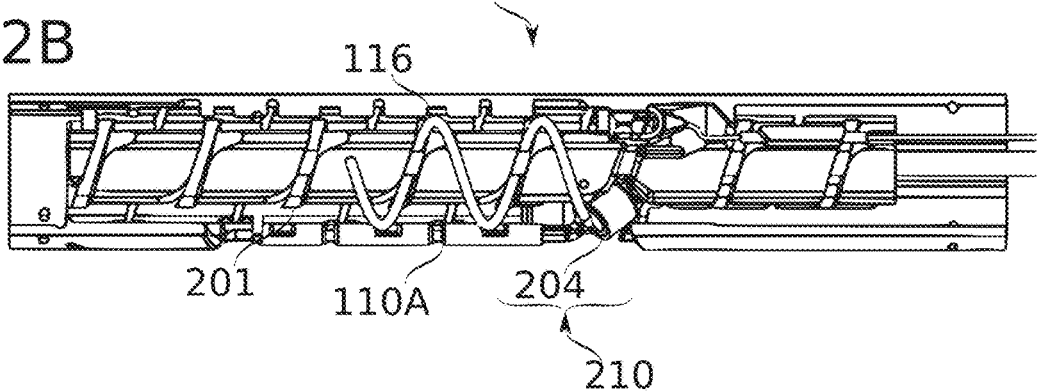
Figure 2C:
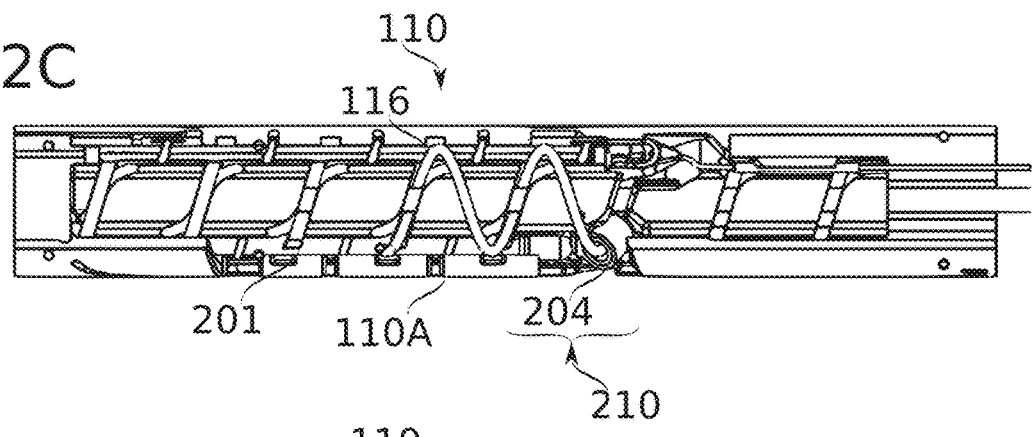
Figure 2D:
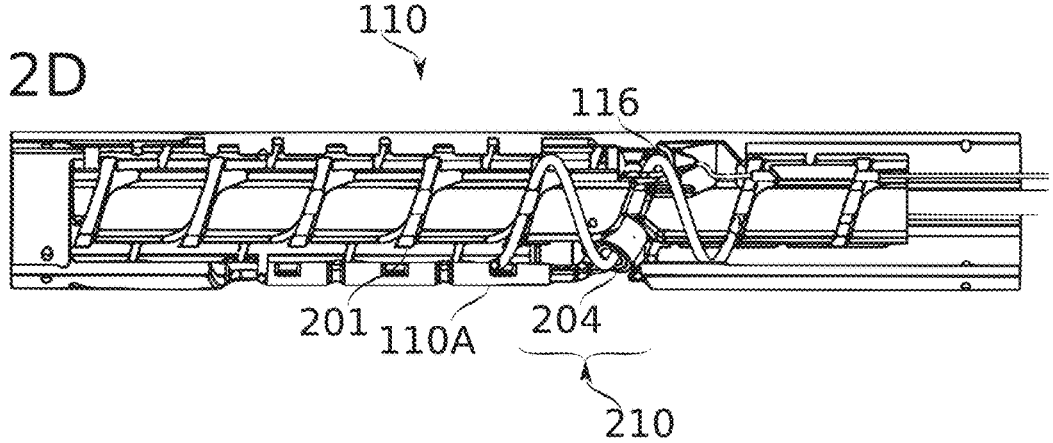

In FIG. 2B, needle 116 has advanced to just before the position of suture clip body 204. Suture clip body 204 is oriented so that advancing needle 116 enters it (FIG. 2C) as a consequence of continuing its helical forward motion, and, moreover, continues to pass through it without interference with further helical forward motion (FIG. 2D).

Figure 2E:
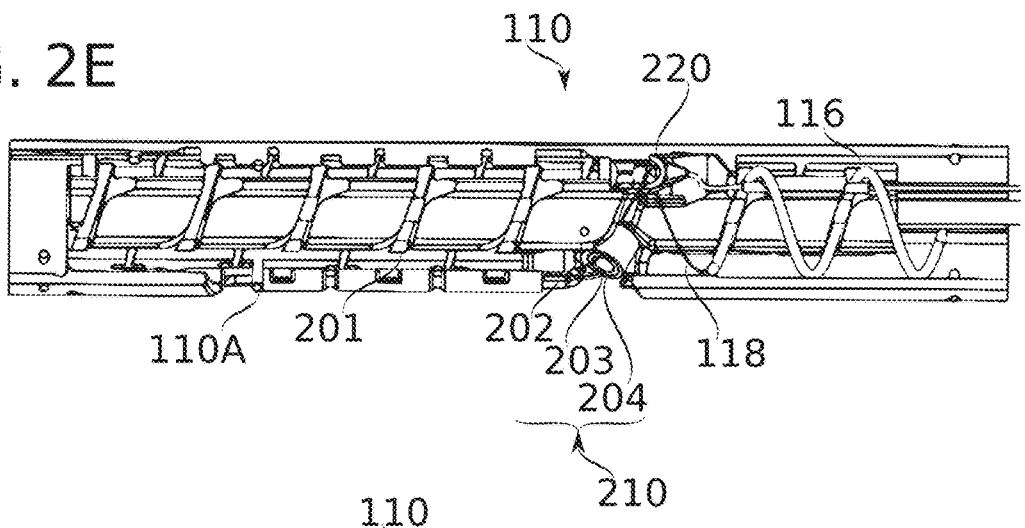
FIGS. 2E-2G schematically represent stages in clamping of suture clip to a suture, according to some embodiments of the present disclosure.

It is noted that display of suture 118 is suppressed in FIGS. 2A-2D; it is normally attached to a trailing end of needle 116, for example as shown in FIG. 2E.

Figure 2F:
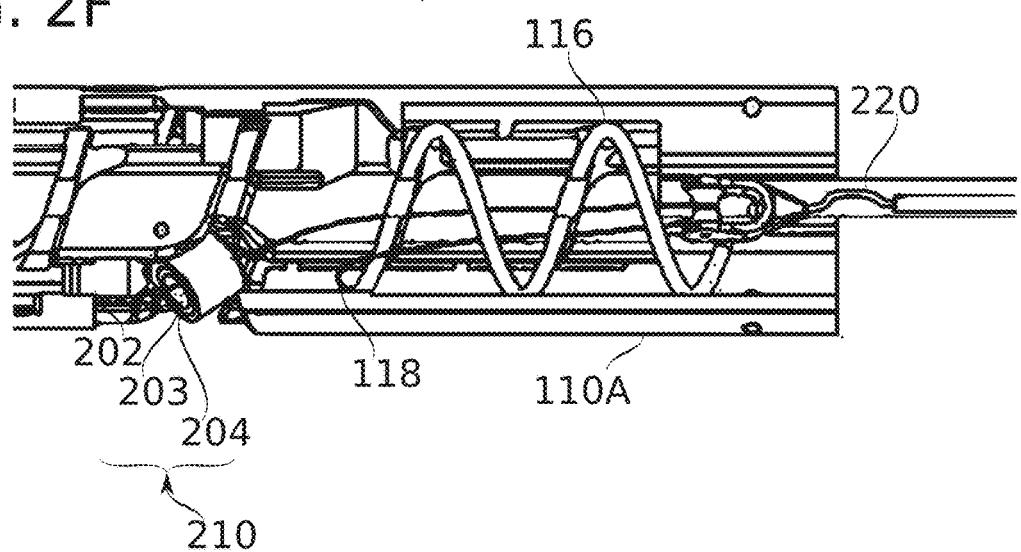
Figure 2G:
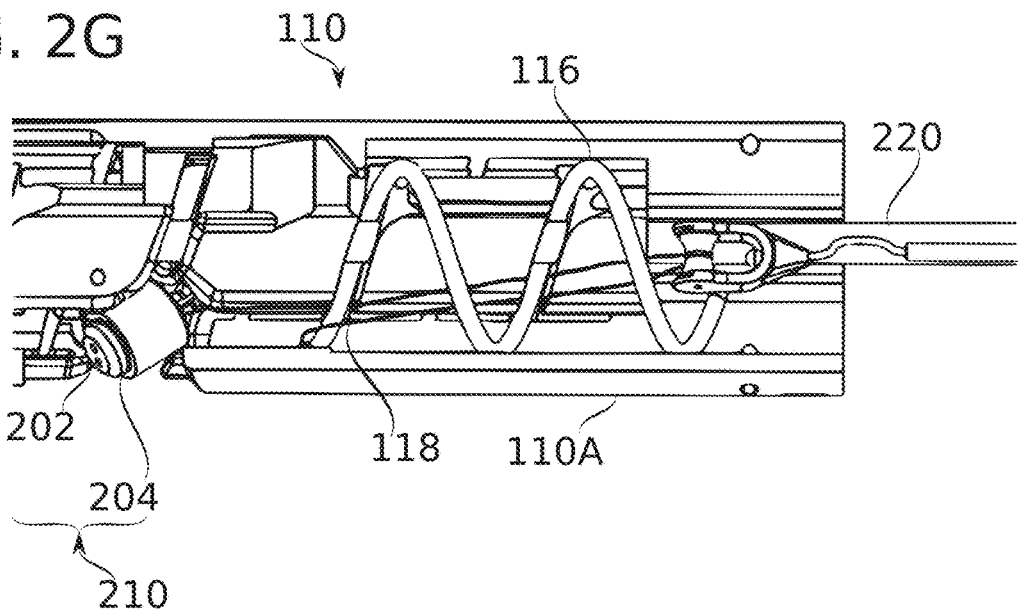

Reference is now made to FIG. 2E-2G, which schematically represent stages in clamping of suture clip 210 to a suture 118, according to some embodiments of the present disclosure. Suture clip 210 is a more particular example of a suture clip 130.

In FIG. 2E (continuing from the configuration of FIG. 2D), needle 116 is now fully advanced through suture clip body 204, such that suture line 118, attached to a trailing side of needle 116, is now threaded through suture clip body 204. Needle 116 has also advanced through an aperture of suture tightener 220 (described further, for example in relation to FIGS. 3A-3B and/or 5A-5D).

Exemplary Suture Tightening and Clamping

Figure 3A:
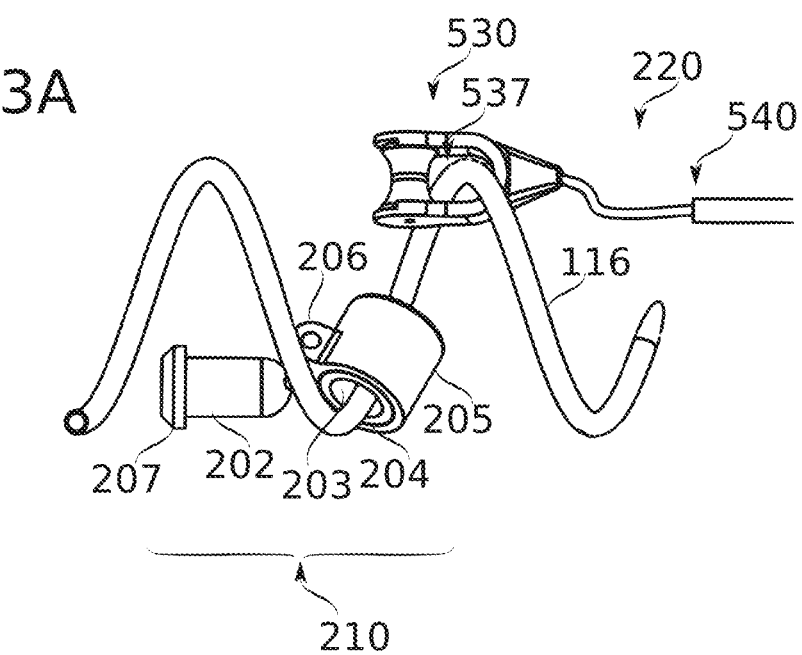
FIG. 3A shows detail of needle, in a position where it is passing by helical advance through both clip body, and an aperture of tightening head of suture tightener, according to some embodiments of the present disclosure.

Brief reference is made to FIG. 3A, which shows detail of needle 116, in a position where it is passing by helical advance through both clip body 204, and an aperture 537 of tightening head 530 of suture tightener 220, according to some embodiments of the present disclosure. It is noted in particular that clip body 204 is held within the predetermined pathway of needle 116 by clip case 206 (which is in turn attached to the bougie 100, optionally fixedly attached). Tightening head 530, also, is initially positioned at a position within the bougie along a predetermined path of needle 116. It is not fixedly positioned, however; for example, it can be pulled proximally by exerting tension on control member 540.

Figure 3B:
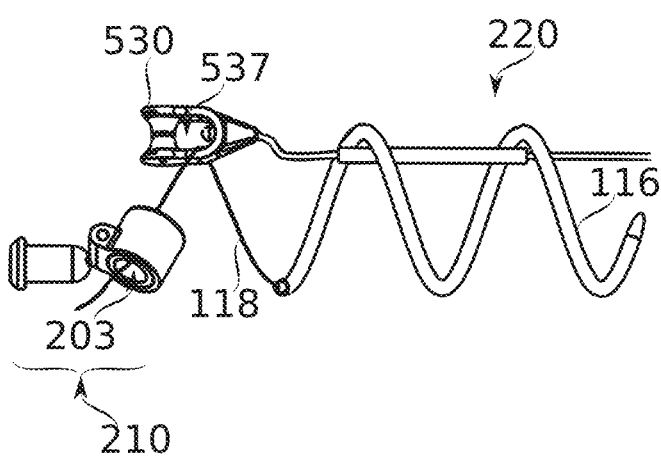
FIG. 3B shows detail of needle, in a position where it has already passed by helical advance through both clip body, and an aperture of tightening head of suture tightener, according to some embodiments of the present disclosure.

Brief reference is also made to FIG. 3B, which shows detail of needle 116, in a position where it has already passed by helical advance through both clip body 204, and an aperture 537 of tightening head 530 of suture tightener 220, according to some embodiments of the present disclosure. Suture 118 trails behind needle 116, and is now threaded through aperture 537 of the tightening head 530, and through aperture 203 of the suture clip 210.

In FIG. 2F, suture 118 has been drawn short by proximal movement of suture tightener 220. Needle 116 acts as an anchor for one end of suture 118, so that as suture-threaded suture tightener 220 is pulled proximally, slack is taken out of the stitches left behind by the passage (e.g., helical passage) of needle 116 through tissue 50.

As the suture slack is taken out of the stitches, the suture line is also pulled further past and/or through suture clip 210. It is noted that although suture clip 210 has already captured the suture line (e.g., the suture line has been threaded through it), it has not yet clamped it, so it the sliding movement of the suture is not interfered with.

In some embodiments, clamping of suture clip 210 (shown in FIG. 2G) comprises moving clip plug 202 into an aperture 203 of clip body 204, for example as described in relation to FIGS. 4A-4D.

Figure 3C:
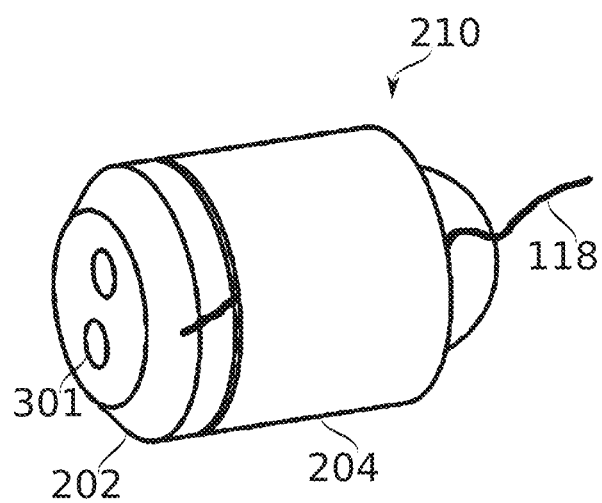
FIG. 3C shows clip plug and clip body of suture clip in a clamped configuration, according to some embodiments of the present disclosure.

Brief reference is made to FIG. 3C, which shows clip plug 202 and clip body 204 of suture clip 210 in a clamped configuration, according to some embodiments of the present disclosure. Suture 118 extends within clip body 204, and between clip body 204 and clip plug 202. Also shown are holes 301; used in manipulating clip plug 202 to produce clamping, for example as explain in relation to FIGS. 4A-4D, herein.

Reference is now made to FIGS. 4A-4D, which schematically represent components and clamping mechanism of a cylindrically clamping suture clip 210, according to some embodiments of the present disclosure. Aspects of suturing clip operation applicable, for example, to suture clip 210 are also described, for example, in relation to FIGS. 2A-2G and 3A-3C.

Figure 4A:
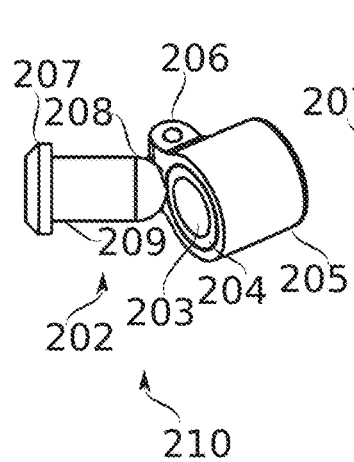
FIGS. 4A-4D schematically represent components and clamping mechanism of a cylindrically clamping suture clip, according to some embodiments of the present disclosure.
Figure 4B:
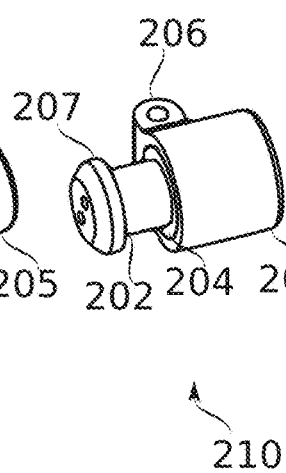
Figure 4C:
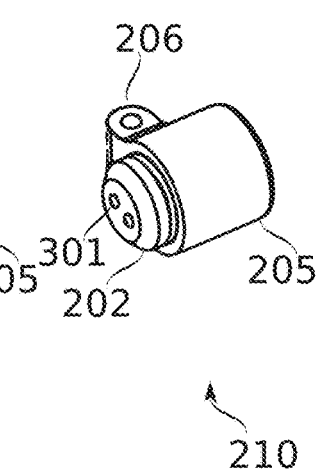

Suturing clamp 210, in some embodiments, comprises a clip plug 202 and a clip body 204, into which clip plug 202 is fittingly insertable (e.g., as shown in the sequence of FIGS. 4A-4C). The fitted portion comprises clamping portion 209, which presses against an inner wall of aperture 203 of clip body 204. When a suture 118 is threaded through aperture 203, clamping portion 209 and/or clip body 204 are loose and/or elastic enough to fit together even over the obstruction presented by the suture 118; in some embodiments, the elastic deformation of the clip body 204 and/or clip plug 202 induced as a result contributes to clamping forces on suture 118. In some embodiments, clamping portion 209 comprises a parallel cylindrical outer wall.

An aspect of the operation of suturing clip 210 is that its clamping is actuatable by manipulation of a control member (e.g., control member 120) from a position remote from the suturing clip 210 (e.g., the suturing clip 210 can be closed by pulling on a wire or cord portion outside the body, while suturing clip 210 itself is still inside a cavity of the body, and inside bougie 100). The control member passes through aperture 203 between clip plug 202 and a control member portion on which pulling force is exerted, so that shortening the control member brings the clip plug 202 and clip body 204 together.

In some embodiments, clip plug 202 is configured for remote actuation by embodying one or more of a plug guide tip 208, hole(s) 301, and insertion stop 207.

Plug guide tip 208, in some embodiments, is located at an inserting end of clip plug 202, and is rounded and/or tapered to make clip plug 202 self-centering as it is advanced into aperture 203.

One or more holes 301, in some embodiments, are optionally open on both ends, and extend along a longitudinal axis of clip plug 202. Holes 301 accept insertion of a control member (not shown in the figures) thereto, and optionally therethrough. Optionally, the control member is anchored to the clip plug 202, and later released, e.g., by cutting. Alternatively, in some embodiments, a plurality of holes is configured to allow a control member to pass into the clip plug 202 from, e.g., the end comprising the plug guide tip 208, out the other end, then back in the same end and out again on the end comprising the plug guide tip 208. When both ends of the control member are pulled on at the same time, the clip plug is urged into the aperture 203 of the clip body 204. If one control member end is released and the other is pulled on, the control member eventually slips entirely through both of the holes it is threaded to, releasing itself from the clip.

Insertion stop 207, in some embodiments, comprises a widening on the trailing side of the insertion plug 202, which prevents plug 202 from being pulled entirely through aperture 203 and out the other side.

In some embodiments, clip case 205 holds and positions clip body 204 within bougie 100. For example, clip case 205 optionally comprises a mounting protrusion 206 which is attached to the bougie 100, e.g., by a pin, screw, and/or other arrangement.

Figure 4D:
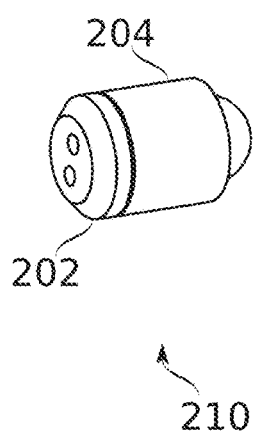
Figure 5A:
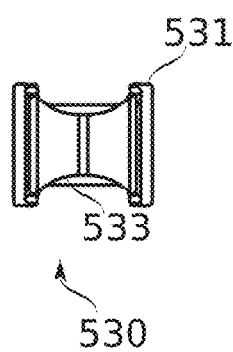
FIGS. 5A-5D schematically represent components and assembled configuration of a suture tightener, according to some embodiments of the present disclosure.
Figure 5B:
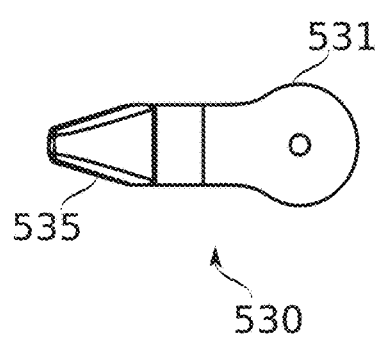
Figure 5C:
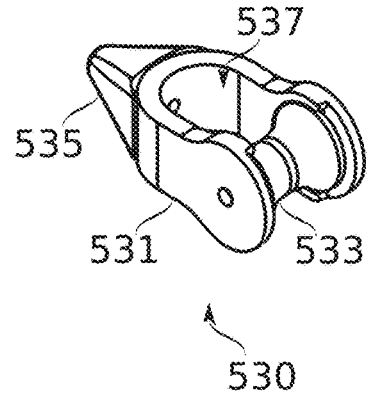
Figure 5D:
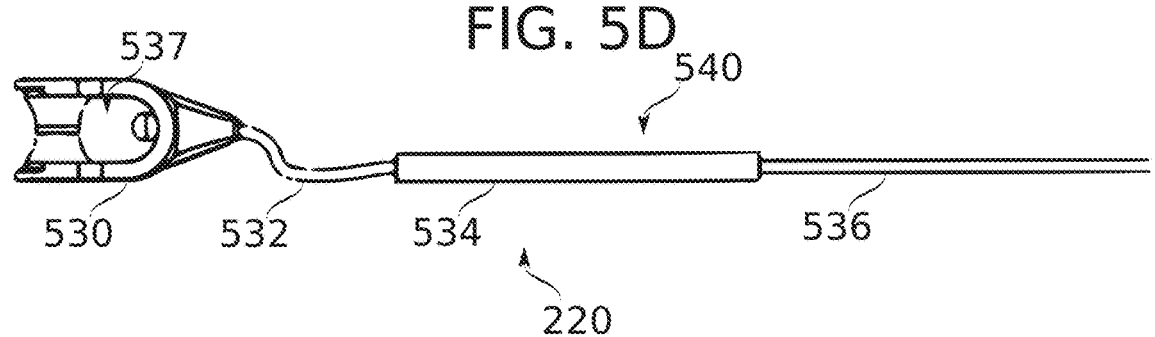

FIG. 4D shows suture clip 210 released from its case 205. In some embodiments, release of suture clip 210 from clip case 205 occurs as a consequence of withdrawing bougie 100 from the body after suture clip 210 is clamped. Tension from the tissue-attached suture retains suture clip 210, so that it separates when bougie 100 is extracted. Optionally, clip case 205 is shaped to obstruct suture clip 210 from exiting on the wrong side, e.g., during clamping.

Reference is now made to FIGS. 5A-5D, which schematically represent components and assembled configuration of a suture tightener 220, according to some embodiments of the present disclosure. Operation of a suture tightener 220 is described, for example, in relation to FIGS. 2E-2G and/or 3A-3B, herein.

Suture tighter 220, in some embodiments, comprises a control member 540 (e.g., an example of a control member 120) and a tightening head 530.

Tightening head 530 is configured to capture (e.g., by threading) suture 118 from a position behind the advance of needle 116, for example by a loop or open-sided suture catcher (e.g., as described herein in relation to suture catcher 132 of a suturing clip). In the example shown, the suture 118 is captured (threaded) when needle 116 pulling an end of suture 118 passes through an aperture 537 defined by a harness 531 and a spindle 533.

Spindle 533 is optionally fixed, or spins to form a pulley. Spindle 533, in some embodiments, is narrower toward the middle, and flared toward the ends. This helps to center the suture 118 under tension, potentially avoiding pulling on it from a sharp interior corner of the tightening head 530, and/or preventing getting caught in a gap between spindle 533 and harness 531. In some embodiments, tightening head 530 is attached to its control member 540 through a strain relief 535. Optionally, strain relief 535 is tapered, for example to assist it in entering a channel of bougie 100 along which tightening head 530 is to be drawn.

Control member 540 optionally comprises a stiffener 534, which extends at least through a region of the bougie traversed by needle 116. Stiffener 534 stiffens control member 540 enough to prevent control member 540 from becoming entangled with needle 116.

Optional flexible (e.g., string or wire-like) distal section 532 of control member 540 attaches between tightening head 530 and stiffener 534. Being flexible, it allows tightening head 530 to self-adjust its position and orientation according to the direction of pull from suture 118 during tightening. Being short, entanglement with needle 116 is potentially avoided. Proximal section 536 of control member 540 optionally comprises a wire, string, cable, or other construction. Optionally, the proximal and distal sections 532, 536 join or are comprised in a single piece underneath stiffener 534.

In some embodiments, cutting suture 118 is performed using a tool of an endoscope inserted through the bougie. Optionally, cutting suture 118 is performed using sharpened edge placed in the bougie 100 at a position that allows it to be pressed against, clamped over, and/or sawed on the suture, at a position between a suturing clip 130 and needle 116. For example, the sharped edge is placed partially across an interior space of bougie 100 on a distal side of the fully advanced needle 116. As the bougie 100 is withdrawn, the suture 118 is stretched between the needle 116 and a suture clip 130. Once it is stretched, the bougie is moved to bring the sharpened edge against the suture 118, cutting it. In some embodiments, the suturing clip 130 itself comprises a cutting edge.

Exemplary Rotating-Clamp Suture Clip

Reference is now made to FIGS. 6A-6D, which schematically represent a suture clip 600 which clips by a rotational movement, according to some embodiments of the present disclosure.

Suture clip 600, in some embodiments comprises clip body 620, clip insert 610, and optionally clip stopper ring 630. Clip insert 610 attaches with clip body 620 by means of screw threads 613 that mate with screw threads inside clip body 620. Clip body 620 is held attached to bougie body 110A, e.g., by the fitted insertion of protrusions 623 into receiving locations of bougie body 110A, or by another method.

Mounted within the bougie, suture clip 600 is positioned with apertures of holes 611 (of clip insert 610) and 622 (of clip body 620) aligned with each other, and moreover aligned with a predetermined path of needle 116, so that needle 116 passes into the holes 611, 622 as it advances; for example as shown in FIG. 6D. Clip body 620 may be said to have two holes—each opposite each other on the wall of the clip body 620.

After passage of needle 116 through holes 611, 622, suture clip 600 may be operated to clamp suture 118. For this, hole 611 is rotated relative to holes 622 (out of alignment with them), for example in direction 640. This distorts the suture 118, and pulls it around within clip body 620 where it is clamped between the threads of clip body 620 and clip insert 610. Optionally, clip stopper ring 630 is attached to an end of clip insert 610, and prevents over-rotation.

Rotational force is optionally exerted by rotation of a control member 650 (an example of a control member 120). Control member 650 mates, for example, with a distal end 615 of insert 610. Keying protrusion 617 mates with a matching notch in a socketed end of the control member 650, to allow rotational force to be transmitted.

Suture clip 600, once clamped to suture 118, optionally slides out of its receiving locations upon removal of the bougie from the body cavity, due, e.g., to being retained by stitches made using suture 118.

Optionally, an edge of one or more of holes 611, 622 is sharpened. Optionally, rotating to clamp also severs suture 118 on the proximal side. Optionally, rotating by itself does not sever suture 118; rather the suture must also be held tight, e.g., stretched using a suture tightener 220.

Exemplary Sensor Arrangements and Operation

Figure 13:
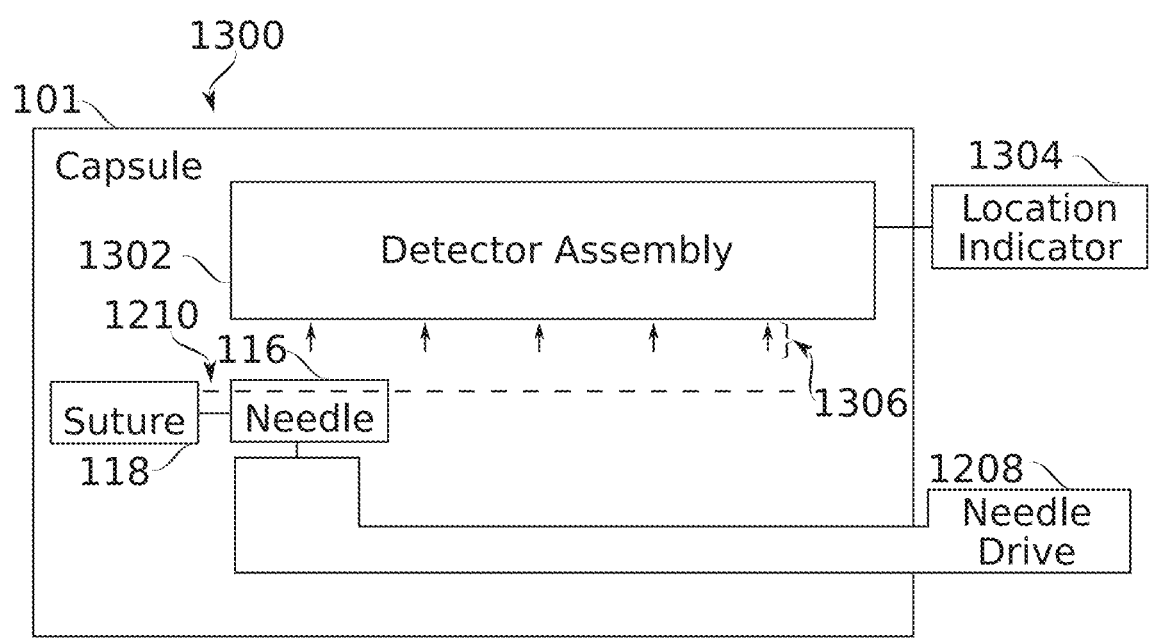
FIG. 13 schematically represents a needle position sensing subsystem of an intrabody suturing device, according to some embodiments of the present disclosure.

Reference is now made to FIG. 13, which schematically represents a needle position sensing subsystem 1300 of an intrabody suturing device, according to some embodiments of the present disclosure.

Position sensing subsystem 1300, in some embodiments, comprises a detector assembly 1302 positioned along needle path 1210 within a capsule section 101 of a suturing bougie. Needle 116 is configured to move along a path 1210 (e.g., actuated by needle drive 1208) pulling suture 118. The path 1210 may be helical. Detector assembly 1302 is configured to detect the presence, arrival, and/or departure of needle 116 at a plurality of positions 1306 along path 1210. Location indicator 1305 interprets signals from detector assembly and provides an indication of a current location of needle 116 accordingly.

Position sensing subsystem 1300, in some embodiments, allows tracking and/or confirmation of needle movements actuated by needle drive 1208. A potential advantage of this is that needle drive 1208 need not itself be deterministic in how its own movements are translated into movement of needle 116. For example, there can be slippage and/or hysteresis in the interaction between needle drive 1208 and needle 116. Position sensing subsystem 1300 provides positive feedback that motion has actually occurred, and/or indications of how much motion has occurred. Sensing subsystem 1300 optionally comprises a single elongated sensor, or a plurality of sensors; implemented, for example, as described in relation to FIGS. 7A-9D, herein.

Reference is now made to FIGS. 7A-7D, which schematically represent a pressure sensor arrangement for measuring movements and/or positioning of a needle 116, according to some embodiments of the present disclosure.

In some embodiments of the present disclosure, a suction clamping domain 110 is provided with sensing for determining the presence and/or position of a needle 116. In some embodiments, the needle 116 is helical, and sensing is provided which allows per-turn sensing of the advance of the helical needle. Needle presence and/or position sensing provides a potential advantage in particular for verifying that the needle has passed the suction clamping domain 110, e.g., so that further steps such as suture tightening and suture clip clamping are not performed before the stitches are fully in place.

It is a potential advantage, moreover, to know how far along the needle 116 is in its advance; for example, if it becomes stuck or slowed during advance, corrective action may be taken sooner, if there is position sensing resolution more detailed than "suturing completed/suturing not-completed". In some embodiments, needle position is measured in steps with the width of a helical winding, for example by sensing discretely at 2, 3, 4, 5, or more locations. Needle positions are optionally distinguished by a pattern of activated sensors. For example: initially none of four sensors along a longitudinal axis of helical advance. As the needed advances, one, two, three, then four sensors are activated. As the needle advances further, the trailing sensors deactivate one-by-one, until three, two, one, then no sensors are activated. Thus, in this example, eight different needle positions are identified. It should be understood that a different number of sensors is optionally used, and that sensors are optionally active at the beginning or end of the needle movement. Optionally, sensor lines are placed on the needle path at either side of the bougie body 110A, allowing finer sensing resolution. Sensor activation patterns are optionally sensed, for example, by receiving individual inputs from each sensor, or by sensing a cumulative input from several sensors (for example, as detailed in relation to the pressure sensor of FIGS. 7A-7D).

In some embodiments, a needle position sensor 700 comprises a flexible tube 705 extending longitudinally along bougie body 110A. Tube 705 is attached to a pressure sensor 710 (e.g., at one end of the tube), and the other end of tube 705 is sealed. Accordingly, compressing tube 705 causes the sensed pressure to rise. Tube 705 is held in place (e.g., by fastening tubes 704) so that needle 116 compresses it at intermittent sensing locations 702 as it moves (e.g., helically advances) along its predetermined path. Optionally, needle 116 directly presses an overlaying cover 703 at each sensing location 702, and cover 703 in turn compresses tube 705. Potential advantages of this include: cover 703 can be shaped to ensure that it protrudes enough into the interior of the bougie body 110 to be pressed against; cover 703 can be shaped to ensure that needle 116 presses it to the side instead of piercing it; cover 703 can be made longer than the width of needle 116 so that more of tube 702 is compressed (producing a larger pressure change).

Sensor indicator 712 indicates needle position status based on readings from pressure sensor 710. Sensor indicator 712 optionally comprises a LED indicator, e.g., with a segment lit per sensing position 702 triggered. Optionally, sensor indicator 712 indicates position using tones. Optionally, sensor indicator 712 comprises a user interface for a computer configured to show a graphical and/or visual indication based on signals transmitted from pressure sensor 710.

Optionally, a step in pressure change is registered by sensor 710 (and optionally displayed by sensor indicator 712) for each sensing location 702 at which needle 116 begins pressing against tube 705. This allows sensing the advance of needle 116, first as sensing locations 702 are sequentially pressed against (increasing pressure), and then as sensing locations 702 are sequentially relieved of pressure.

Optionally, pressure sensor 710 reports small (less than a step-sized) variations in pressure as well. Optionally, sensor indicator 712 displays these small variations, which may provide hints to the device operator about needle state. For example, if the needle drive is repeatedly slipping at a particular part of the rotation cycle, there may be a corresponding (potentially small) change in pressure indication as force on the needle redistributes. An operator can respond, for example, by changing the way that advancing is controlled, and/or adjusting angulation and/or bending of the device, using the pattern of pressure changes as a guide to the effect of such adjustments. Even without slippage, there is potentially seen a pattern in pressure readings which correlates to when a needle is beginning to press against the next tissue layer, when it is sliding through it, and/or when it has successfully passed it. Optionally, the device operator adjusts operations to advance the needle and/or manipulate the angulation and/or bending of the bougie itself, based in part on such patterns.

It is noted that certain suture tighteners themselves may be used as sensors. Once a needle 116 has entered the aperture of a suture tightener, the suture tightener is partially locked into place, preventing free operation until the needle is past it again. Testing of this condition by use of gentle tugs may be used additionally or alternatively with use of dedicated sensors to determine the position of the needle 116.

Reference is now made to FIGS. 8A-8C, which schematically represent a magnetic sensor arrangement for measuring movements and/or positioning of a needle 116A, according to some embodiments of the present disclosure.

In some embodiments, magnetic field sensors 802 (e.g., Hall effect sensors) are mounted, e.g., on a circuit board 800, which in turn mounts to bougie body 110A of suction clamping domain 110. The sensors 802 are preferable placed at the location of closest approach by needle 116A. Needle 116A is magnetized, e.g., along its whole length (it is optionally embodied, for example, as a needle 116 which has been magnetized). As needle 116A approaches each sensor 802 in turn, the sensor 802 registers a change in magnetic field, outputting a signal which in turn is sensed by a signal processing circuit 810, producing a position indication displayed by sensor indicator 812 (which may produce indications, e.g., as described for sensor indicator 810, suitably adjusted for magnetic signals rather than pressure signals).

The signals produced by sensors 802 are optionally processed and/or displayed as "present" or "not present" indications of needle proximity. Additionally or alternatively, signals components produced by sensors 802 with less than the size of a whole step are processed and/or displayed, e.g., as effectively continuous-value signals (for example, analog signals and/or digital signals encoded with a bit depth of several bits, e.g., 5 or more bits). Stresses and/or strains placed on needle 116 to advance it potentially change its shape slightly as it moves, for example as described in relation to the embodiments of FIG. 7A-7D. Nearby magnetic field sensors 802 may in turn fluctuate slightly in the signals they produce. Indications of such fluctuations are optionally used by a device operator to guide device operation, for example as described in relation to FIGS. 7A-7D.

Reference is now made to FIGS. 9A-9D, which schematically represent a circuit board-based sensor arrangement for measuring movements and/or positioning of a needle 116A, according to some embodiments of the present disclosure.

In some embodiments, sensor board 900 comprises a circuit board configured with a plurality of leads 901A, 901B, 901C, 901D connected to a sensing circuit 910. A portion of each lead extends along an edge 904 of sensor board 900, each along a different longitudinal portion of sensor board 900.

In some embodiments, each lead 901A-901D has a characteristic impedance associated with it, which changes when the lead is shortened. Additionally or alternatively, an end of each lead is connected to ground (e.g., from the other side of circuit board 900, not shown).

Sensor board 900 is positioned on bougie body 110A of suction clamping domain 110 at a position where a tip 902C of needle 116 sequentially impinges, as it helically advance, on each individual lead 901A-901D near edge 904 in turn. The impinging in turn breaks the impinged on lead. Optionally board 900 is weakened near the position of impingement 903 so that a notch is knocked out of the board upon impingement.

Sensing circuit 910 senses the change in impedance and/or opening of the grounded circuit, providing a signal which sensor indicator 912 in turn indicates, for example as described in relation to sensor indicator 712.

Additionally or alternatively, in some embodiments, leads 901A-901D comprise a foil, spring, or other conductive element which needle 116 contacts (and optionally deforms and/or breaks) as it rotates. Electrical contact may be established thereby between the different leads through needle 116, and this contact used as the basis for position sensing (by sensing circuit 910) and indicating (by sensor indicator 712). Optionally, conductance across the area of electrical contact is subject to minor variability as the needle moves. This variation itself optionally comprises an indication of needle movement.

Optionally, needle 116 is at least partially coated with an insulating polymer (for example, on side 902D, compared to side 902E which may be left uncoated). The polymer coating is optionally interrupted at intervals to expose the metal. In some embodiments, this is used to allow the needle 116 to act as an encoder of its own progress, by counting events of making and/or breaking electrical contact as coated and uncoated needle portions pass over the sensor.

It is noted that a sensor at a single position can be used with such a needle 116, e.g., by providing it with two contacts (and sensing conduction between them through the needle), or by providing it with one contact and creating a circuit that passes through the body of the needle to a conductor that maintains electrical contact with the needle, such as a wire attached to the needle, or a driver cable used to drive the needle. To track needle 116 over a distance longer than its own length, a plurality of such sensors are optionally provided.

Figure 10:
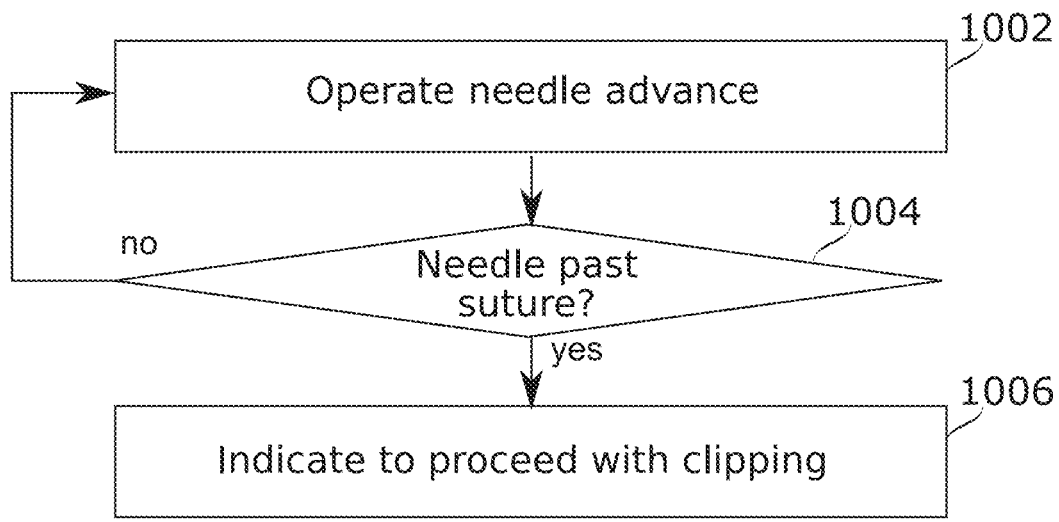
FIG. 10 is a schematic flowchart of a method of guiding suture clip placement within a bougie, according to some embodiments of the present disclosure.

Reference is now made to FIG. 10, which is a schematic flowchart of a method of guiding suture clip placement within a bougie 100, according to some embodiments of the present disclosure.

At block 1002, in some embodiments, a needle positioned inside a body cavity is advanced. The advance is in turn controlled, in some embodiments, by operation of a control member outside the body cavity. Optionally, the needle is helical, positioned within a needle-guiding device such as a bougie 100. The needle advances, in some embodiments, by operation (e.g., rotation) of a control member that drives the needle along a predetermined path defined by the needle-guiding device.

One or more sensors are positioned along the predetermined path, and sense the presence of the needle; for example, according to one of the embodiments of FIGS. 7A-9D.

At block 1004, in some embodiments, it is checked (e.g., by circuitry connected to the sensors) if the needle is past the region that it is configured to suture. In some embodiments, the check comprises verifying that the needle has first been sensed by at least one sensor, but now is no longer sensed by that sensor (that is, the needle has passed the sensor). Additionally or alternatively, a sensor is placed far enough along the predetermined path (e.g., about the length of the needle, measured along its direction of longitudinal travel) so that when a front portion of the needle is sensed, a back portion of the needle has passed the suturing region.

At block 1006, in some embodiments: if the needle is not yet past the suture region, the flowchart returns to block 1002. Otherwise, an indication is provided that the procedure can continue; e.g., with clamping of a suture clip, for example as described herein relation to blocks from block 158 onward in FIG. 1C.

Figure 11:
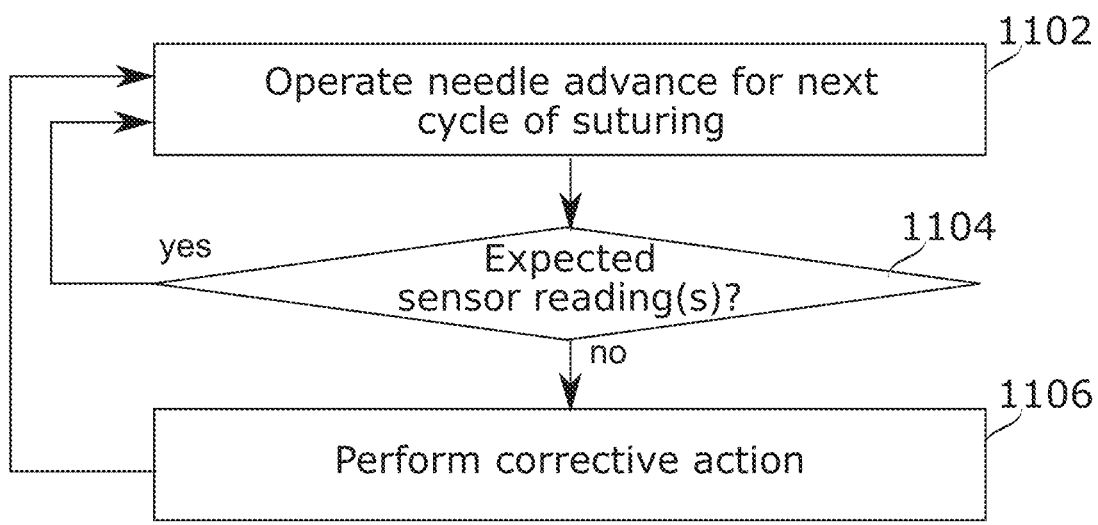
FIG. 11 is a schematic flowchart of a method of guiding needle advance along a bougie, according to some embodiments of the present disclosure.

Reference is now made to FIG. 11, which is a schematic flowchart of a method of guiding needle advance along a bougie 100, according to some embodiments of the present disclosure.

At block 1102, in some embodiments, a needle positioned inside a body cavity is advanced by operation of a control member outside the body cavity. The configuration of the bougie 100 and needle is, for example, as described in relation to FIG. 10. The operation to advance the needle is performed to an extent which is considered likely to bring the needle into sensing range of a sensor (and/or move it out of sensing range of a sensor) of the bougie 100. For example, if there is a sensor placed spaced at each turn of a helical needle, then the control member is optionally operated sufficiently that it is anticipated to advance the helical needle by about a turn, assuming that there is no restraint on needle advance that prevents this. Optionally, operation of the control member is also sensed, for example using an encoder 121A.

At block 1104, in some embodiments, it is checked if the needle has indeed reached and/or moved out of sensing range of the sensor(s), according to the anticipated result. If so, then the procedure returns to block 1102 and continues with further advancing of the needle.

Otherwise, at block 1106, a corrective measure is taken. This may comprise, for example, one or more of:
  Reversing the direction of needle travel.
  Adjusting the needle drive (e.g., longitudinally translating a needle drive cable so that a different part of it works on the needle).
  Otherwise changing how force is exerted to induce needle travel (e.g., operating the needle advancing control member more quickly or more slowly).
  Changing an angulation of the bougie 100, e.g., to change forces exerted on the needle.
  Changing bending of the bougie 100, e.g., to change forces exerted on the needle.

After and/or while the corrective measure is taken, the flowchart returns to block 1102. The flowchart continues until it is no longer necessary to advance the needle, e.g., until the result of block 1004 of FIG. 10 indicates to proceed with clipping.

General

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the present disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments may be presented with reference to a range format. It should be understood that the description in range format is merely for convenience and brevity and should not be construed as an inflexible limitation on the scope of descriptions of the present disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although descriptions of the present disclosure are provided in conjunction with specific embodiments, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting. In addition, any priority document(s) of this application is/are hereby incorporated herein by reference in its/their entirety.

It is appreciated that certain features which are, for clarity, described in the present disclosure in the context of separate embodiments, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

What is claimed is:

1. A bougie configured for placing suturing in a body cavity wall, the bougie comprising:
   a vacuum clamping domain, sized for insertion into the body cavity, and comprising surfaces defining an interior space, and apertures into the interior space configured to receive tissue of the body cavity wall upon application of suction thereto;
   a needle within the interior space, with suture attached to the needle; and
   a suture clip within the interior space;
   wherein the needle is actuatable to translate along a path within the interior space while carrying the suture through the tissue; and
   wherein the suture clip is positioned to capture the suture at a position along the path, and operable to clamp the captured suture
   wherein said bougie comprising a suture tightener at least partially within the interior space, said suture tightener also positioned to capture the suture at a position along the path, and operable, from outside the bougie, to move to apply a pulling force on the suture to reduce a length of tissue-engaged suture; and
   the suture tightener comprises an aperture positioned along the path, and the suture tightener captures the suture when the needle pulls the suture through the aperture of the suture tightener.

2. The bougie of claim 1, wherein the suture clip comprises a suture-catching aperture, and the path extends through the suture-catching aperture.

3. The bougie of claim 1, wherein the needle comprises a helical needle, the path comprises a helical path along which the helical needle translates by rotation, and the suture clip is positioned along the helical path.

4. The bougie of claim 1, wherein a suture catching portion of the suture clip is configured so that after capture of the suture, the suture remains free to loosely translate longitudinally past the suture clip.

5. The bougie of claim 1, wherein the suture clip comprises a plurality of clamping portions, and the suture is clamped by movement of the clamping portions closer to one another.

6. The bougie of claim 5, wherein the clamping portions are configured to insert one inside another, and the clamping movement comprises inserting one clamping portion inside another clamping portion.

7. The bougie of claim 5, wherein the clamping movement comprises rotating one of the plurality of clamping portions with respect to another one of the plurality of clamping portions.

8. The bougie of claim 7, wherein the rotating comprises moving apertures of one of the plurality of clamping portions out of alignment with at least another one of the plurality of clamping portions.

9. The bougie of claim 1, comprising a plurality of sensing positions, positioned along the path, each sensing position configured with a sensor configured to sense the adjacent presence of the needle.

10. The bougie of claim 9, wherein each sensing position has a separate respective sensor.

11. The bougie of claim 9, wherein the sensor comprises at least one of the group consisting of:
    a pressure sensor,
    an impedance sensor of impedance of an electrical conductor,
    a contact sensor of contact with an electrical conductor,
    a breakage sensor of breakage of an electrical conductor, and
    a Hall effect sensor.

12. The bougie of claim 9, wherein the plurality of sensing positions share a single sensor.

13. The bougie of claim 9, wherein the needle comprises a helical needle, the path comprises a helical path along which the helical needle translates by rotation, and the plurality of sensing positions are also arranged along a longitudinal axis of the vacuum clamping domain.

14. The bougie of claim 1, wherein the suture captured by the suture tightener slides freely with respect to the suture tightener while the suture tightener moves to reduce the length of tissue-engaged suture.

15. The bougie of claim 14, wherein the suture tightener, when moved to reduce the length of tissue-engaged suture, doubles over the suture so that both ends of the suture are on a same side of the suture tightener.

16. The bougie of claim 15, wherein the suture tightener comprises a spindle over which the suture is doubled over.

17. The bougie of claim 16, wherein the spindle is narrower toward a middle of the spindle than at ends of the spindle.

18. The bougie of claim 16, wherein the spindle is rotatably mounted to the suture tightener.

19. A bougie configured for placing suturing in a body cavity wall, the bougie comprising:
    a vacuum clamping domain, sized for insertion into the body cavity, and comprising surfaces defining an interior space, and apertures into the interior space configured to receive tissue of the body cavity wall upon application of suction thereto;
    a needle within the interior space, with suture attached to the needle; and
    a suture clip within the interior space;
    wherein the needle is actuatable to translate along a path within the interior space while carrying the suture through the tissue; and
    wherein the suture clip is positioned to capture the suture at a position along the path, and operable to clamp the captured suture
    wherein said bougie comprising a suture tightener at least partially within the interior space, said suture tightener also positioned to capture the suture at a position along the path, and operable, from outside the bougie, to move to apply a pulling force on the suture to reduce a length of tissue-engaged suture;

wherein the suture captured by the suture tightener slides freely with respect to the suture tightener while the suture tightener moves to reduce the length of tissue-engaged suture; and wherein the suture tightener, when moved to reduce the length of tissue-engaged suture, doubles over the suture so that both ends of the suture are on a same side of the suture tightener.

\* \* \* \* \*